United States Patent [19]
Tsien et al.

[11] Patent Number: 5,661,035
[45] Date of Patent: Aug. 26, 1997

[54] VOLTAGE SENSING BY FLUORESCENCE RESONANCE ENERGY TRANSFER

[75] Inventors: Roger Y. Tsien; Jesus E. Gonzalez, III, both of La Jolla, Calif.

[73] Assignee: The Regents of the University of California, Oakland, Calif.

[21] Appl. No.: 481,977

[22] Filed: Jun. 7, 1995

[51] Int. Cl.$^6$ ................................................ G01N 21/64
[52] U.S. Cl. .......................... 436/63; 436/172; 435/29; 435/173.4
[58] Field of Search ................ 436/63, 172; 435/29, 435/173.4

[56] References Cited

U.S. PATENT DOCUMENTS

| | | | |
|---|---|---|---|
| 4,560,665 | 12/1985 | Nakae et al. | 436/172 |
| 4,647,531 | 3/1987 | Kamentsky | 435/7 |
| 5,169,788 | 12/1992 | Chen et al. | 436/172 |

FOREIGN PATENT DOCUMENTS 1231884 of 0000 United Kingdom.

OTHER PUBLICATIONS

Lakey, J.H. "Fluroescence Energy Transfer Distance Measurements" *J. Mol. Biol.* vol. 230, pp. 1055–1067 (1993).

Fung, B.K. et al. "Surface Density Determination in Membranes by Fluorescence Energy Transfer" *Biochemistry*, vol. 17, No. 24, pp. 5241–5248 (1978).

Waggoner, A. S. and Grinvald, A. 1977. Mechanisms of rapid optical changes of potential sensitive dyes. *Ann.N.Y.Acad. Sci.* 303:217–241.

Grinvald, A., Frostig, R.D., Lieke, E., and Hildesheim, R. 1988. Optical imaging of neuronal activity. *Physiol. Rev.* 68:1285–1366.

Salzberg, B.M. 1993. Optical recording of electrical activity in neurons using molecular probes. In Current Methods in Cellular Neurobiology, J.L. Barker, editor. Wiley, New York. 139–187.

Cohen, L.B. and S. Lesher. 1985. Optical monitoring of membrane potential: methods of multisite optical measurement. In Optical Methods in Cell Physiology, P. de Weer and B.M. Salzberg, editors. Wiley, New York. 71–99.

Loew, L.M. 1988. How to choose a potentiometric membrane probe. In Spectroscopic Membrane Probes. L.M. Loew, editor, CRC Press, Boca Raton. 139–151.

Loew, L.M. 1993. Potentiometric membrane dyes. In Fluorescent and Luminescent Probes for Biological Activity. W.T. Mason, Editor. Academic, San Diego. 150–160.

Benz, R. and Conti, F. 1981. Structure of the squid axon membrane as derived from charge–pulse relaxation studies in the presence of absorbed lipophilic ions. *J. Membrane Biol.* 59:91–104.

Benz, R. and Nonner, W. 1981. Structure of the axolemma of frog myelinated nerve: relaxation experiments with a lipophilic probe ion. *J. Membrane Biol.* 59:127–134.

(List continued on next page.)

*Primary Examiner*—Jeffrey Snay
*Attorney, Agent, or Firm*—Townsend & Townsend & Crew LLP

[57] ABSTRACT

Compositions and methods for use in generating fast ratiometric voltage-sensitive fluorescence changes in single or multiple cells systems. A first reagent is a membrane-bound hydrophobic fluorescent anion which rapidly redistributes from one face of the plasma membrane to the other in response to the transmembrane potential, as described by the Nernst equation. A voltage-sensitive fluorescent readout is created by labeling the intracellular or extracellular surface of the cell with a second reagent comprising a fluorophore which can undergo energy transfer with the first reagent or a quencher for the first reagent. Quenching or FRET between the two reagents is disrupted when the membrane potential is depolarized, because the anionic first reagent is pulled to the intracellular surface of the plasma membrane far from the asymmetrically bound second reagent. In preferred embodiments of the invention, the first and second reagents are bound together by a suitable linker group.

6 Claims, 9 Drawing Sheets

OTHER PUBLICATIONS

Fernández, J.M., Taylor, R.E., and Bezanilla, F. 1983. Induced capacitance in the squid giant axon. *J. Gen. Physiol.* 82:331–346.

Benz, R. 1988. Structural requirement for the rapid movement of charged molecules across membranes. *Biophys. J.* 54:25–33.

Flewelling, R.F. and Hubbell, W. L. 1986. The membrane dipole potential in a total membrane potential model. *Biophys. J.* 49:541–552.

Bortnick, N., Luskin, L.S., Hurwitz, M.D., and Rytina, A.W. 1956. t–Carbinamines,RR'R"CNH$_2$. III. The preparation of isocyanates, isothiocyanates and related compounds. *J. Am. Chem. Soc.* 78:4358–4361.

Henderson, S.A., Spencer, M., Sen, A., Kumar, C., Siddiqui, M.A.Q., and Chien, K.R. 1989. Structure organization, and expression of the rat cardiac myosin light chain–2 gene. *J. Biol. Chem.* 264:18142–18146.

Savitsky, A. and Golay, M.J.E. 1964. Smoothing and differentiation of data by simplified least squares procedure. *Anal. Chem.* 36:1627–1639.

Tsien, R.Y. and B.J. Bacskai. 1994. Video–rate confocal microscopy. In Handbook of Biological Confocal Microscopy. J.B. Pawley, editor. Plenum Press, New York.

Weber, G. and Teale, F.W.K. 1957. Determination of the absolute quantum yield of fluorescent solutions. *Faraday Soc. Trans.* 53:646–655.

Wu, P. and Brand, L. 1994. Resonance energy transfer: methods and applications. *Anal. Biochem.* 218:1–13.

Rink, T. J., Montecucco, C., Hesketh, T.R., and Tsien, R.Y. 1980. Lymphocyte membrane potential assessed with fluorescent probes. *Biochim. Biophys. Acta* 595:15–30.

Hodgkin, A. 1975. The optimum density of sodium channels in an unmyelinated nerve. *Philos. Trans. R. Soc. Lond.* [*Biol*] 270:297–300.

Ketterer, B., Neumcke, B., and Läuger, P. 1971. Transport mechanism of hydrophobic ions through lipid bilayer membranes. *J. Membrane Biol.* 5:225–245.

Andersen. O.S. and Fuchs, M. 1975. Potential energy barriers to ion transport within lipid bilayer. *Biophys. J.* 15:795–830.

Benz, R., Läuger, P., and Janko, K. 1976. Transport kinetics of hydrophobic ions in lipid bilayer membranes. *Biochim. Biophys. Acta* 455:701–720.

Conforti, L., Tohse, N., and Sperelakis, N. 1991. Influence of sympathetic innervation on the membrane electrical properties of neonatal rat cardiomyocytes in culture. *J. Devel. Physiol.* 15:237–246.

Hill, B.C. and Courtney, K.R. 1982. Voltage–sensitive dyes discerning contraction and electrical signals in myocardium. *Biophys. J.* 40:255–257.

Montana, V., Farkas, D.L., and Loew, L.M. 1989. Dual–wavelength ratiometric fluorescence measurements of membrane potential. *Biochemistry* 28:4536–4539.

Grinvald, A., Fine, A., Farber, I.C., and Hildesheim, R. 1983. Fluorescence monitoring of electrical responses from small neurons and their processes. *Biophys. J.* 42:195–198.

VOLTAGE SENSING BY FLUORESCENCE RESONANCE ENERGY TRANSFER

This invention was made with Government support under Grant No. R01 NS27177-07, awarded by the National Institutes of Health. The Government has certain rights in this invention.

BACKGROUND OF THE INVENTION

The present invention relates generally to the fields of biology and chemistry. In particular, the present invention is directed to compositions and methods for use in voltage sensing, especially in biological systems.

Fluorescence detection and imaging of cellular electrical activity is a technique of great importance and potential [Grinvald, A., Frostig, R. D., Lieke, E., and Hildesheim, R. 1988. Optical imaging of neuronal activity. *Physiol. Rev.* 68:1285–1366; Salzberg, B. M. 1983. Optical recording of electrical activity in neurons using molecular probes. In Current Methods in Cellular Neurobiology. J. L. Barker, editor. Wiley, New York. 139–187; Cohen, L. B. and S. Lesher. 1985. Optical monitoring of membrane potential: methods of multisite optical measurement. In Optical Methods in Cell Physiology. P. de Weer and B. M. Salzberg, editors. Wiley, New York. 71–99]. Mechanisms for optical sensing of membrane potential have traditionally been divided into two classes: sensitive but slow redistribution of permeant ions from extracellular medium into the cell, and fast but small perturbations of relatively impermeable dyes attached to one face of the plasma membrane [Loew, L. M. 1988. How to choose a potentiometric membrane probe. In Spectroscopic Membrane Probes. L. M. Loew, editor. CRC Press, Boca Raton. 139–151; Loew, L. M. 1993. Potentiometric membrane dyes. In Fluorescent and Luminescent Probes for Biological Activity. W. T. Mason, editor. Academic, San Diego. 150–160].

The permeant ions are sensitive because the ratio of their concentrations between the inside and outside of the cell can change by up to the Nernstian limit of 10-fold for 60 mV change in transmembrane potential. Their responses are slow because to establish new equilibria, ions must diffuse, through unstirred layers in each aqueous phase and the low-dielectric-constant interior of the plasma membrane.

By contrast, the impermeable dyes can respond very quickly because they need little or no translocation. They are insensitive, however, because they sense the electric field with only a part of a unit charge moving less than the length of the molecule, which in turn is only a small fraction of the distance across the membrane. Furthermore, a significant fraction of the total dye signal comes from molecules that sit on irrelevant membranes or cells and that dilute the signal from the few correctly placed molecules.

It is an object of the present invention to provide compositions and methods which do not suffer from all of the drawbacks of the prior art.

SUMMARY OF THE INVENTION

Pursuant 16 the present invention, compositions and methods are provided for use in generating fast ratiometric voltage-sensitive fluorescence changes in single or multiple cells systems. A first reagent is a membrane-bound hydrophobic fluorescent anion which rapidly redistributes from one face of the plasma membrane to the other in response to the transmembrane potential, as described by the Nernst equation. A voltage-sensitive fluorescent readout is created by labeling the intracellular or extracellular surface of the cell with a second reagent comprising a fluorophore which can undergo energy transfer with the first reagent or a quencher for the first reagent. Quenching or FRET between the two reagents is disrupted when the membrane potential is depolarized, because the anionic first reagent is pulled to the intracellular surface of the plasma membrane far from the asymmetrically bound second reagent. In preferred embodiments of the invention, the first and second reagents are bound together by a suitable linker group.

BRIEF DESCRIPTION OF THE DRAWINGS

The invention may be better understood with reference to the accompanying drawings, in which.

DEATAILED DESCRIPTION OF THE PREFERRED EMBODIMENTS

Figure 1A:
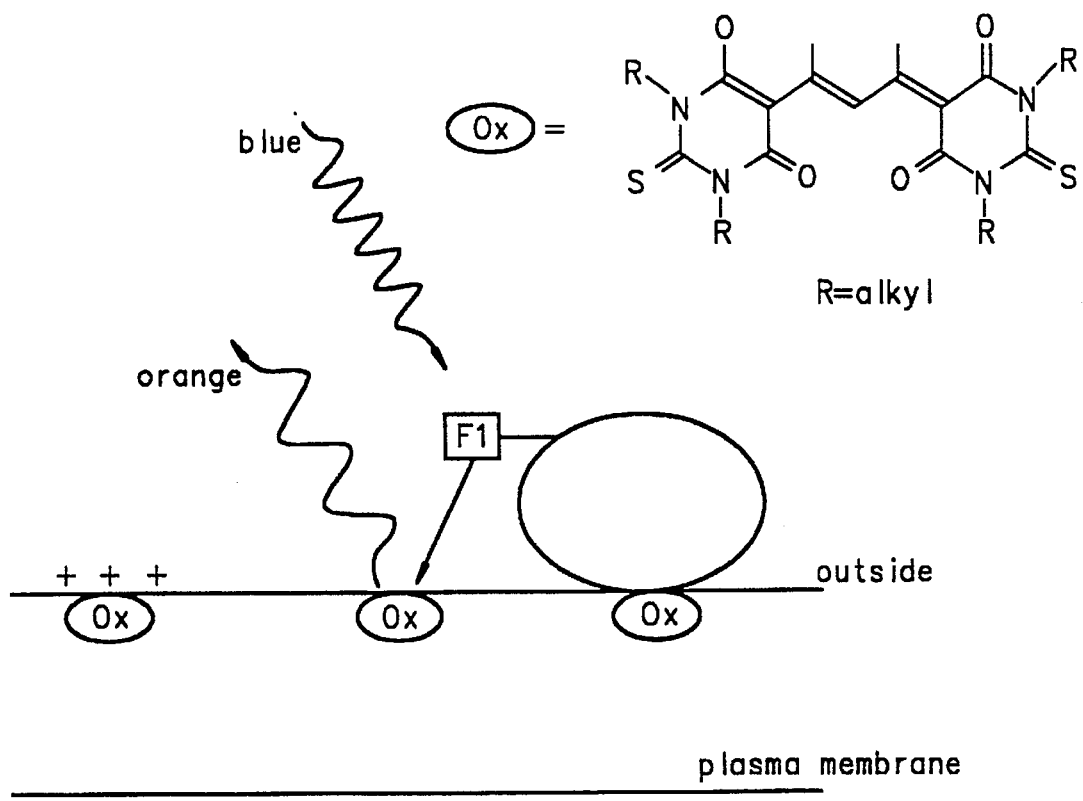
FIGS. 1A and 1B illustrate a scheme of the voltage-sensitive FRET mechanism.

In accordance with the present invention, compositions and methods are provided for use in generating fast ratiometric voltage-sensitive fluorescence changes in single or multiple cells systems. The compositions of the present invention comprise two reagents. The first reagent is a membrane-bound hydrophobic fluorescent anion which rapidly redistributes from one face of the plasma membrane to the other in response to the transmembrane potential. The second reagent comprises a fluorophore which can undergo energy transfer with the first reagent or a quencher for the first reagent. FRET or quenching between the two reagents is disrupted when the membrane potential is depolarized.

In preferred embodiments of the invention, the first and second reagents are bound together by a suitable linker group.

In one class of embodiments of the present invention, the hydrophobic ion fluorescence on one face of the membrane is quenched by a mechanism other than FRET. Although FRET is theoretically the best method, simple quenching could also produce a useful product.

The second fluorophore/quencher can be located on either the intracellular or the extracellular face, as long as it is specific to one or the other. In the specific examples reported herein, the extracellular surface was targeted for convenience.

The voltage-sensitive fluorescence mechanism described herein offers significant advantages compared with previously known mechanisms for optical sensing of potential [Loew 1988, supra; Loew 1993, supra]. The biggest advantage is that a 60 mV change could give in principle up to a 10-fold change in concentration ratio of the mobile dye at the two membrane interfaces, with response times eventually in the submillisecond domain. The optical signals should be correspondingly large, assuming that the FRET or fluorescence/quenching system and emission ratioing can distinguish the two populations of the mobile fluorophore.

In particular, FRET using a fluorescent acceptor inherently offers an emission ratio change that is well suited to laser-scanning confocal microscopy and internally corrects for variations in donor loading, cell thickness and position (including motion artifacts), and excitation intensity. If emission ratioing is not desirable or possible, either wavelength can still be used alone, or the change in donor excited-state lifetime monitored.

Molecular specificity for particular cell types in a mixed population may be introduced by using cell-specific antibodies or adhesion molecules as the carriers of the extracellular fluorescent label. Specifically labeled cells also reduce background staining and maintain the large fluorescence changes in complex tissue.

To achieve high sensitivity, the voltage sensor should translocate at least a full unit charge nearly all the way through the membrane. Even without specific ion channels or transporters, such translocation can be quite rapid if the ion is negatively charged, delocalized, and hydrophobic. For example, the lipid-soluble non-fluorescent anion of dipicrylamine (2,2',4,4',6,6'-hexanitrodiphenylamine) produces displacement currents in excitable tissue with submillisecond kinetics, comparable in speed to sodium channel gating currents [Benz, R. and Conti, F. 1981. Structure of the squid axon membrane as derived from charge-pulse relaxation studies in the presence of absorbed lipophilic ions. *J. Membrane Biol.* 59:91–104; Benz, R. and Nonner, W. 1981. Structure of the axolemma of frog myelinated nerve: relaxation experiments with a lipophilic probe ion. *J. Membrane Biol.* 59:127–134; Fernández, J. M., Taylor, R. E., and Bezanilla, F. 1983. Induced capacitance in the squid giant axon. *J. Gen. Physiol.* 82:331–346]. However, voltage sensing should not require further diffusion of the ion through the unstirred aqueous layers, because that slows the response tremendously and generates a sustained leakage current.

To create an optical readout from the translocation of the fluorescent membrane-bound ion (i.e., the first reagent) from one side of the plasma membrane to the other side, FRET or fluorescence quenching between the translocating ions and a fluorophore or quencher (i.e., the second reagent) fixed to just one face of the plasma membrane is employed. Most conveniently, the extracellular face is employed.

Figure 1B:
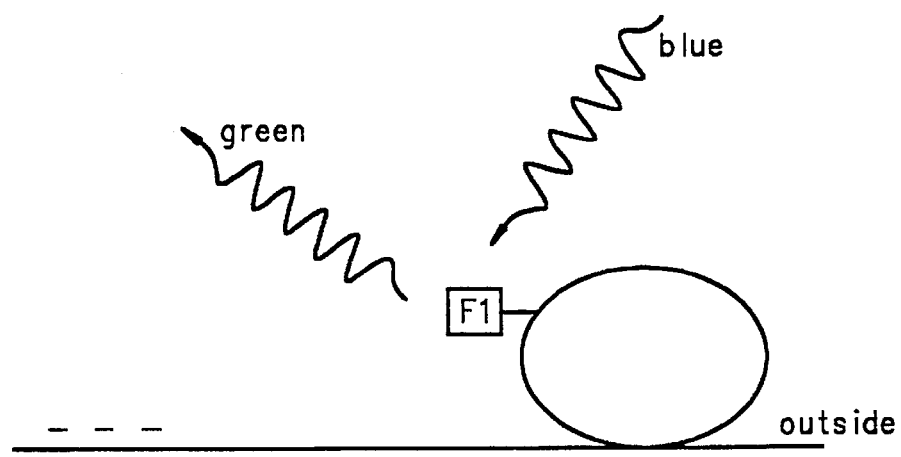
Figure 1B:
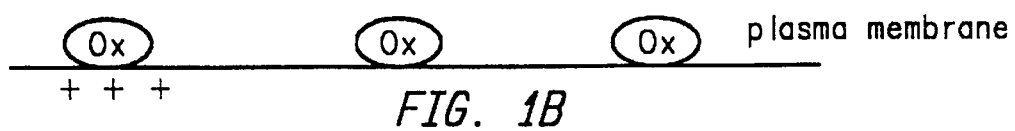

The case where the translocating ions are anionic fluorescent acceptors which absorb at wavelengths that overlap with the emission spectrum of the extracellularly fixed donor fluorophores is schematically shown in FIG. 1. At a resting negative membrane potential (A) permeable oxonols have a high concentration at the extracellular surface of the plasma membrane and energy transfer from the extracellularly bound FL-WGA is favored. FRET is symbolized as the straight arrow from lectin to oxonol. At a positive membrane potential (B) the anions are located primarily on the intracellular surface of the membrane and energy transfer is greatly reduced because of the increased mean distance from the donors on the extracellular surface.

Figure 5:
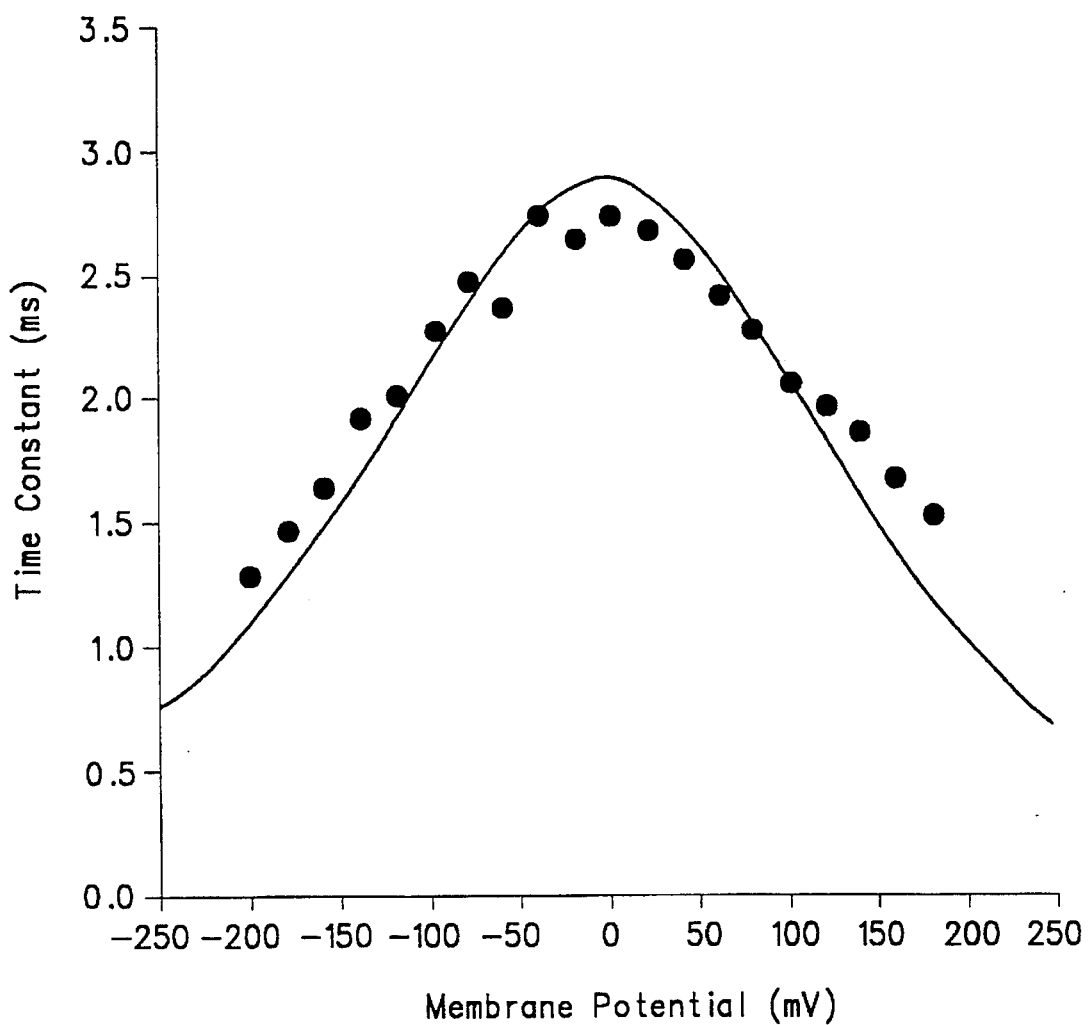
FIG. 5 illustrates voltage dependence of DiSBA-$C_6$-(3) displacement ctirrent time constants in L-M(TK$^-$)cells for the same data shown in FIG. 4.

The speed of the voltage-sensitive fluorescence response depends on the translocation rate of the fluorophore from one site to the other. The speed of response for $DiSBAC_6(3)$ is shown in FIG. 5 and follows the general equation (2). For this reason, the fluorescent ion used as first reagent is central to the present invention. It was critical to develop and design fluorescent ions which jump across the membrane on a millisecond timescale. Slower-jumping ions would not be useful, for example, in following fast electrical signals in neuronal tissue (a primary application of the compositions and methods of the present invention). The development and discovery of such molecules with the added constraint of being fluorescent is not trivial.

All previously reported voltage-sensitive fluorescent indicators operating by potential-driven redistribution of the fluorophore across the membrane had response times of >100 ms, often as long as minutes. An important feature of the present invention is the provision of highly fluorescent dye molecules which translocate across the membrane with unprecedentedly short time constants (e.g., less than <5 ms) and which give identical optical respone times when paired with a second fluorophore or quencher. Response times of <1 ms are necessary for accurate measurement of single action potentials in individual neurons and are obtainable with the very fastest of the dyes described herein (e.g., hexyl-substituted pentamethineoxonol). The best characterized examples have response times in the 2–5 ms range, which is fast enough to monitor voltage changes in heart and smooth muscle, many synaptic potentials in single neurons, and the average firing activity in populations of neurons (for example, mapping the electrical responses of different regions of the central nervous system to sensory inputs). The indicators of the present invention are more than fast enough to follow voltage changes in nonexcitable cells and organelles, which typically occur over a time scale of seconds to minutes.

In principle, the permeant ions could be donors rather than acceptors. Each of the alternatives has its own advantages. An example with the permeant ion being the FRET donor is the $DiSBAC_6(3)$/Texas Red WGA combination. A primary advantage of this arrangement is that it minimizes the concentration of the dye molecule in the membrane; this reduces toxicity and cellular perturbations resulting from the displacement current and any photodynamic effects. Another advantage is the generally higher quantum yields of fluorophores bound in membranes relative to those on proteins or water; this gives better FRET at a given distance.

The motion of the mobile anions generates a displacement current, which might represent a significant capacitative shunt in some cases. The obvious remedy in such cases is to use as low a loading of mobile anion as possible, decreasing ttie concentration of the fluorescent ion in the membrane by lowering the concentration thereof in the bath. In order to maintain a sufficient surface density of acceptors to give adequate energy transfer efficiency, it is theoretically preferable for the mobile anions to be the donors and the fixed labels to be the acceptors in stoichiometric excess; having the donor in the membrane minimizes the necessary amount of dye needed for efficient FRET or quenching.

Further, in accordance with particularly preferred embodiments of the present invention, it is advantageous to tie the two together with a tether long enough to span the entire membrane (i.e., a linker group as hereinafter defined). This makes the optical response characteristics independent of absolute acceptor concentration.

It should be noted that responses may deviate significantly from linearity and saturate for very large voltage changes. Some nonlinearity is inevitable in any sensitive fluorescence mechanism, because fluorescence can neither go negative nor increase without limit. Fortunately, the actual response, a hyperbolic tangent function of voltage, maximizes sensitivity over the physiologically most relevant range of membrane potentials and is mathematically tractable and correctable. Most current applications of fast potentiometric indicators do not attempt to calibrate absolute values of membrane potential.

Bis-(1,3-dialkyl-2-thiobarbiturate)-trimethineoxonols, where alkyl is n-hexyl and n-decyl (DiSBA-$C_6$(3) and DiSBA-$C_{10}$-(3) respectively) have been shown herein to function as donors to Texas Red labeled wheat germ agglutinin (TR-WGA) and as a. cceptors from fluorescein labeled lectin (Fl-WGA). In voltage-clamped fibroblasts, the translocation of these oxonols was measured as a displacement current with a time constant of ~2 ms for 100 mV depolarization at 20° C., which equals the speed of the fluorescence changes. Fluorescence ratio changes of between 4–34% were observed for a 100 mV depolarization in fibroblasts, astrocytoma cells, beating cardiac myocytes, and B104 neuroblastoma cells. The large fluorescence changes allowed high speed confocal imaging.

In the compositions and methods of the present invention, the first reagent comprises a membrane-bound hydrophobic ion (fluorescence donor, acceptor, or quencher) which serves as the voltage sensor and moves in response to the membrane potential. The distribution of the hydrophobic ions between the two membrane-aqueous interfaces is described by the Nernst equation. The inherent sensitivity of the invention is based on the large interfacial concentration changes of the ion with physiologically relevant membrane potentials. Potentially, a 60 mV change could produce 10-fold change in the ratio of interfacial concentrations. If the coupled fluorescent readout is efficient, similarly large fluorescence changes could be realized. The speed of the fluorescence change is dependent on the membrane translocation rate of the hydrophobic ion.

The permeant ions should be highly hydrophobic with a single delocalized charge in order to bind strongly to the plasma membrane and translocate rapidly across it in response to membrane potential. Delocalization of the charge reduces the Born charging energy (inversely proportional to radius) for moving a charged molecule from a hydrophilic to a hydrophobic environment and may be essential for rapid translocation of ions [Benz, R. 1988. Structural requirement for the rapid movement of charged molecules across membranes. Biophys. J. 54:25–33]. Increasing hydrophobicity minimizes release of the bound dye from the plasma membrane and buries the ion deeper into the membrane, which decreases the electrostatic activation energy for translocation. Polar groups on the ion should be kept to a minimum and shielded as much as possible to disfavor solvation in the headgroup region of the bilayer. However, hydrophobicity cannot be increased without limit, because some aqueous solubility is required to permit cellular loading.

Anions have a tremendous inherent speed advantage over cations, because the ester groups of biological membranes generate a sizable dipole potential within the hydrocarbon core of the membrane. This potential aids anion translocation through the hydrophobic layer but hinders cations. It is known that for the isostructural ions tetraphenyl phosphonium cation and tetraphenylborate anion, the anion is much more permeable than the cation [Flewelling, R. F. and Hubbell, W. L. 1986. The membrane dipole potential in a total membrane potential model. Biophys. J. 49:541–552].

The anions should also be strongly fluorescent when adsorbed to the membrane, whereas they should have minimal fluorescence when free in aqueous solution. Preferably, the anionic fluorophores should be at least four times, and more preferably at least about eight times, brighter when adsorbed to the membrane. In the case of the thiobarbiturate oxonols described herein, the selectivity is outstanding with a fluorescence about 20 brighter in the membrane than in water. In principle, if the dye bound extremely tightly to the membrane one would not need any fluorescence selectivity; however, because in reality the volume of the membrane is tiny relative to the aqueous solution and some water solubility is necessary for loading of the dye into cells and tissue, a selectivity greater than 1 is highly desirable and probably necessary for a good dye system.

The anions also should not act as ionophores, especially protonophores, since such behavior would generate sustained leakage currents far more injurious than unavoidable transient displacement currents. Therefore, any protonation pKa must be kept far below 7. Red to infra-red wavelengths of excitation and emission are preferred to avoid tissue scattering and heme absorbances. Photodynamic damage should be kept as low as possible, probably best by minimizing triplet state formation and the resulting generation of singlet oxygen.

Presently preferred fluorescent hydrophobic ions include bis-(1,3-dialkyl-2-thiobarbiturate)-polymethine oxonols and derivatives thereof. These compounds have the general formula

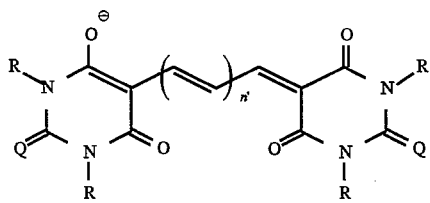

wherein each R is independently selected from the group consisting of alkyl groups of about 4 to about 40 carbon atoms (preferably, about 5 to about 20 carbon atoms), groups of the formula —$(CH_2)_m Q_o (CH_2)_n CH_3$, in which m is an integer from 1 to about 20 (preferably about 15), n is an integer from 1 to about 20 (preferably about 15), o is 0 or 1 and n+m+o together provide a group having a length less than that of an alkyl group comprising about 40 carbon units (preferably less than about 20 carbon units), groups of the formula $(CH_2)_m(CH=CH)_o(CH_2)_n CH_3$ in which m is an integer from 1 to about 20 (preferably about 15), n is an integer from 1 to about 20 (preferably about 15), o is an integer from 1 to about 6 and n+m+o together provide a group having a length less than that of an alkyl group comprising about 40 carbon units (preferably less than about 20 carbon units), and groups of the formula

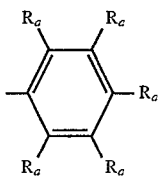

in which each $R_a$ is independently selected from the group consisting of R, halogen and H;

n' is an integer from 1 to 3; and

Q is S or O.

The oxonol's negative charge is distributed over the entire the chromophore. The trimethine oxonols absorb at 542 nm (ext. coef=200,000 $M^{-1}$ $cm^{-1}$), emit at 560 nm and have a quantum yield of 0.4 in octanol. The R=n-hexyl compound translocates with a time constant ($\tau$) <3 ms in voltage clamped mammalian cells and the decyl compound, <2 ms. The molecular requirement for rapid translocation is nicely met with the symmetric oxonols. The pentamethine oxonols absorb at ~630 nm and emit at ~660 nm. The negative charge is further alelocalized in these red-shifted oxonols. As expected, the translocation rates are faster than the trimethine oxonols. The butyl derivative crosses the membrane with $\tau$<3 ms. This is 6 times faster than the trimethine oxonol. The hexyl species translocates with $\tau$<1 ms.

Another useful class of fluorescent hydrophobic ions comprises conjugated tetraaryl borates of the general formula

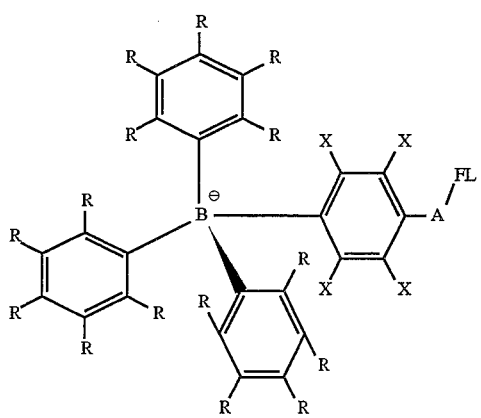

wherein each R is independently selected from the group consisting of H, alkyl groups of 1 to about 40 carbon atoms (preferably, 3 to about 20 carbon atoms), halogen (i.e., Cl, F, Br and I), $CF_3$ and linker groups (as hereinafter defined); each X is independently selected from the group consisting of halogen, $CF_3$ and H; A is O or S; and FL is a neutral fluorophore (as hereinafter defined). A general synthesis of fluorescent borates has been developed, illustrated below for an exemplary fluorescent bimane borate conjugate (identified herein as Bormane, compound IV):

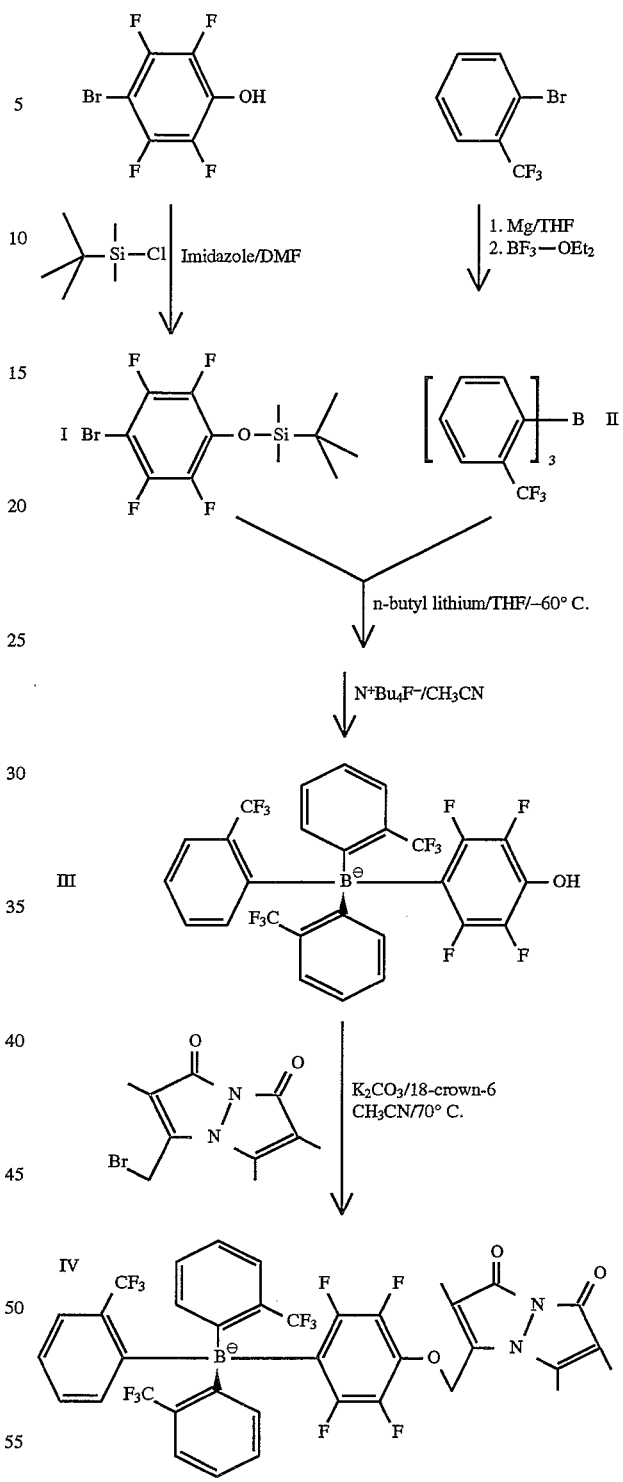

For these ions, a fluorophore is conjugated to a functionalized borate core. This allows one to attach any fluorophore to the borate ion.

As polar chromophores retard the membrane translocation rate, it is preferred that neutral fluorophores be used. For purposes of the present invention, a neutral fluorophore may be defined as a fluorescent molecule which does not contain charged functional groups.

Particularly suitable classes of neutral fluorophores for use in accordance with the present invention include, but are not limited to, the following: bimanes; bodipys; and coumarins.

Bodipys (i.e., difluoroboradiazaindacenes) may be represented by the general formula

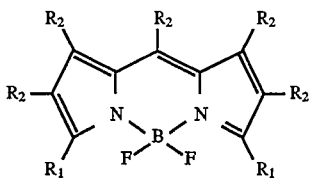

in which each $R_1$ is independently selected from the group consisting of

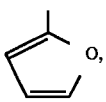

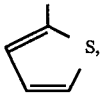

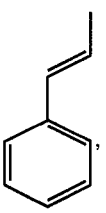

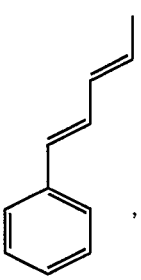

H, lower alkyl, phenyl and an attachment point; and each $R_2$ is independently selected from the group consisting of H, lower alkyl, phenyl and an attachment point.

Coumarins and related fluorophores may be represented by the general formulas

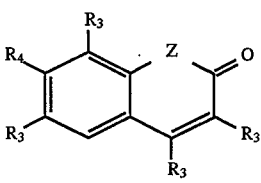

-continued

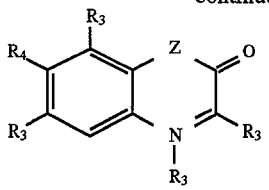

in which each $R_3$ is independently selected from the group consisting of H, halogen, lower alkyl, CN, $CF_3$ and $OR_5$;

$R_4$ is selected from the group consisting of H, $OR_5$ and an attachment point;

$R_5$ is selected from the group consisting of H, lower alkyl and an attachment point; and Z is O, S or $NR_5$.

Bimanes may be represented by the general formula

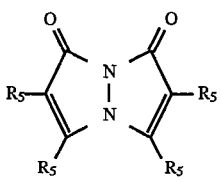

wherein each $R_5$ is independently selected from the group consisting of H, lower alkyl and an attachment point.

Fluorescent tetraaryl borates with coumarins and bimanes attached have been prepared. These fluorescent borates translocate with τ<3 ms in voltage clamped fibroblasts. Synthesis of an exemplary borate is described in Example 2.

The second reagent is a fluorescent donor, acceptor, or quencher which desymmetrizes the two plasma membrane interfaces and generates a fluorescent readout from the hydrophobic ion's movement. As would be immediately apparent to those skilled in the field, there are numerous molecular species which could function as the fluorescently active desymmetrizing agent. The primary characteristics for this component are that it be located on one face of the plasma membrane and function in a complementary manner (i.e., as a fluorescent donor, acceptor, or quencher) with the membrane-bound hydrophobic ion.

Pursuant to the present invention, FRET was first successfully demonstrated with a fluorescent lectin. For purposes of the present invention, a lectin may be defined as a sugar binding protein which when added extracellularly to cells binds to glycoproteins and glycolipids on the extracellular face of the plasma membrane.

Suitable fluorescent groups for use in fluorescent lectins include, but are not limited to, the following: xanthenes (including fluoresceins, rhodamines and rhodols); and cyanines. To date, the best results have been obtained with fluorescein labeled wheat germ agglutinin. (FL-WGA).

One preferred class of second reagents comprises xanthene chromophores of the general formula

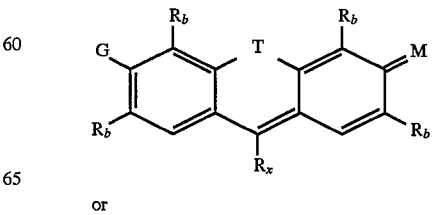

or

-continued

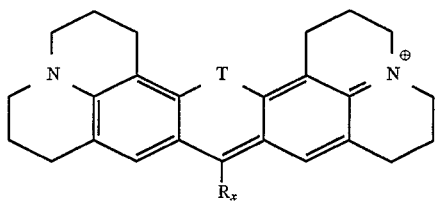

wherein $R_x$ is selected from the group consisting of H, lower alkyl, an attachment point,

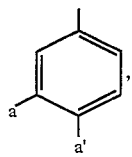

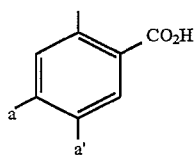

and

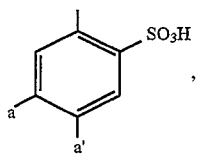

in which each of a and a' is independently selected from the group consisting of H and an attachment point;

each $R_b$ is independently selected from the group consisting of H, halogen, lower alkyl, $SO_3H$ and an attachment point;

G is selected from the group consisting of H, OH, $OR_b$ and $NR_bR_b$;

T is selected from the group consisting of O, S, $C(CH_3)_2$ and $NR_b$; and

M is selected from the group consisting of O and $NR_bR_b$.

Another preferred class of second reagents comprises cyanine dye of the general formula

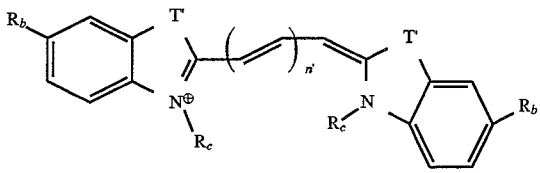

wherein T' is selected from the group consisting of O, S, $C(CH_3)_2$ and $NR_c$; and $R_c$ is selected from the group consisting of H, halogen, lower alkyl, and an attachment point.

Fluorescein labeled amphipathic lipids, in particular phospholipids, have also been successfully employed. For purposes of the present invention, an amphipathic lipid may be defined as a molecule with both hydrophobic and hydrophilic groups that bind to but do not readily cross the cell membrane. Particularly preferred embodiments include fluorescein-labeled phosphatidylethanolamine (FL-PE) and N-(7-nitrobenz-2-oxa-1,3-diazol-4-yl)phosphatidyl ethanolamine (NBD-PE). The fluorescent group is suitably selected from those previously described as useful in preparing fluorescent lectins.

Cytochrome c added to the bath solution has also been found to function as a quencher which binds to the outer plasma membrane leaflet. Accordingly, another suitable class of second reagent comprises cytochrome c or apocytochrome c, with or without a fluorescent group as previously described in connection with other second fluorophores.

Yet another preferred class of embodiments of the second reagent includes fluorescein labeled, amphipathic cyclodextrins which selectively and tightly bind to the extracellular plasma membrane surface. A hydrophobic tail causes tight membrane binding. The cyclic sugar imparts good water solubility for cellular loading and prohibits membrane translocation. Another added benefit is that the cyclodextrins aid the loading of the oxonol.

As would be readily appreciated by those skilled in the art, a wide variety of known donor/acceptor pairs would be available for use in preparing pairs of first and second fluorophores. Particularly preferred combinations include, but are not limited to, the following: fluorescein/trimethine bis-thiobarbiturate oxonol; trimethine bis-thiobarbiturate oxonol/Texas Red; trimethine bis-thiobarbiturate oxonol/resorufin; trimethine bis-thiobarbiturate oxonol/cy5; trimethine bis-thiobarbiturate oxonol/pentamethine bis-thiobarbiturate oxonol; Texas Red/pentamethine bis-thiobarbiturate; and NBD/trimethine bis-thiobarbiturate oxonol.

In some particularly preferred embodiments of the compositions and methods of the present invention, a linker group is employed between the first and second fluorophores. The linker group maintains close proximity between the first and second fluorophores and ensures efficient energy transfer between the donor and acceptor (or fluorophore and quencher) when they are on the same side of the membrane, even at low concentrations. The good energy transfer allows one to separate the donor emission further from the acceptor absorbance and thus decrease the spectral crosstalk that contributes to the reduction of the voltage-sensitive ratio change from theoretical values. Another major advantage of a linker is that it converts the system into a unimolecular phenomenon. This greatly simplifies the fluorescence readout, ensures 1:1 stoichiometry of donor and acceptor (or fluorophore and quencher), and eliminates the need for a critical loading level of donor and acceptor for an optimum voltage-sensitive fluorescence change (with the additional benefit of minimal cellular perturbation and toxicity).

Asymmetric 1,3-substituted thioureas have been prepared for use in synthesizing oxonols with N-substituted linkers containing terminal reactive groups capable of conjugating to appropriate second fluorophores/quenchers. In the example, one of the oxonol substituents is a long alkyl chain (C=12) with a terminal amino group. Thiobarbiturates have been synthesized from these thioureas and diethylmalonate in ethoxide/ethanol. Mixed pentamethine oxonols prepared from 1 equivalent of the barbiturate with the functionalized linker and 1,3-dibutyl thiobarbiturate have been characterized. An exemplary synthesis is depicted below.

Synthesis of Functionalized Oxonols Via Asymmetric Thiourea

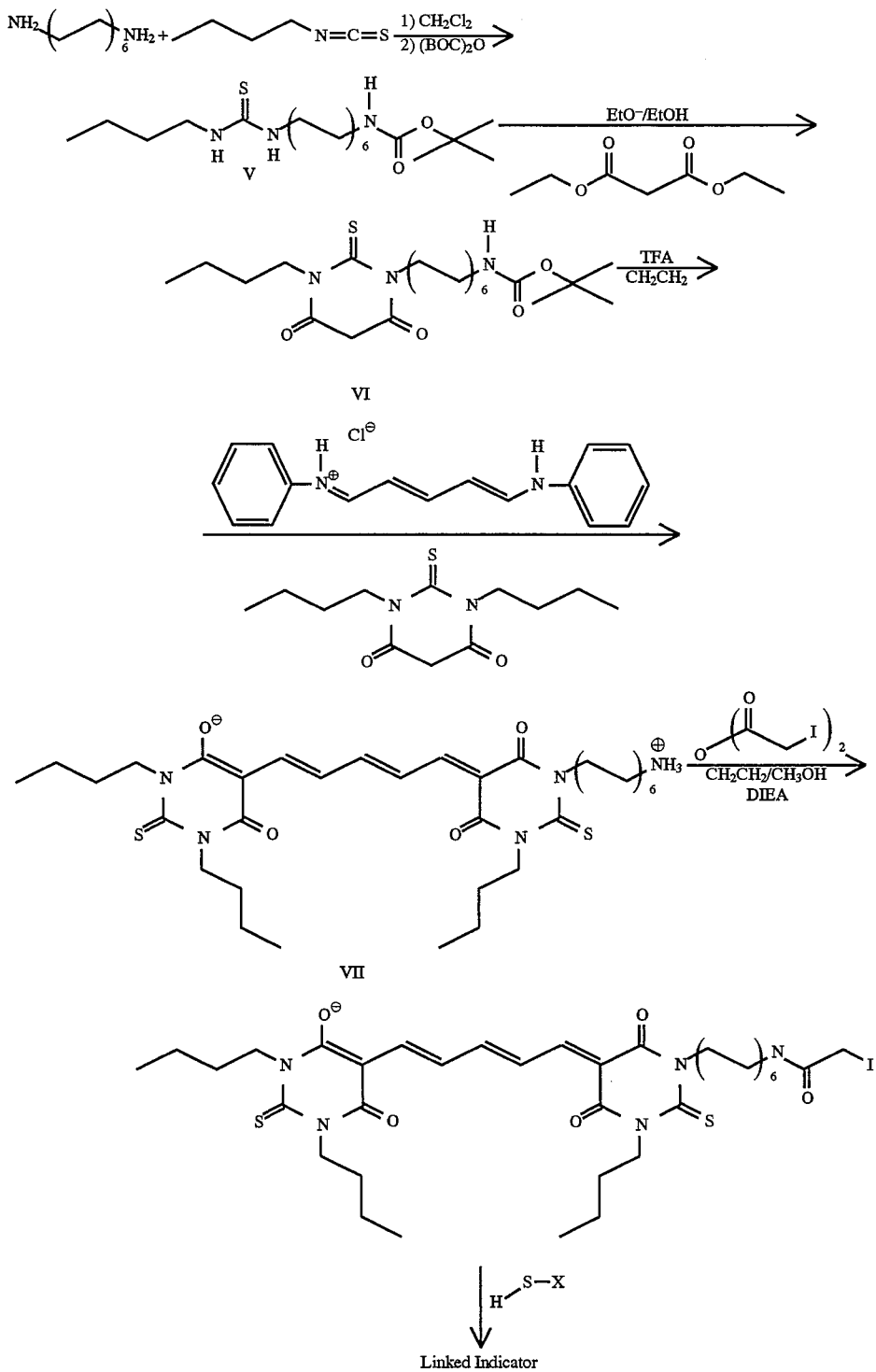

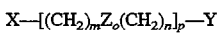

Linked Indicator

One preferred class of suitable linkers includes bi-functionalized polyethylene (polypropylene, polybutylene, etc.) glycol-PEG-oligomers of an appropriate length to span the plasma membrane (25–30 carbon equivalents), for example 8–10 PEG units. The oxygen (or sulfur, in analogs thereof) modulates the hydrophobicity and hence translocation rate and loading. Such linker groups have the general formula $$X\text{—}[(CH_2)_m Z_o (CH_2)_n]_p\text{—}Y$$

in which Z is O or S, m is 0 or an integer from 1 to about 32, n is 0 or an integer from 1 to about 32, o is 0 or 1, p is 0 or an integer from 1 to about 12, the combination of n+m+o+p provides a linker corresponding in length to less than about 36 carbon units, and X and Y are first and second fluorophores, respectively.

Another class of suitable linkers includes functionalized alkyl chains with terminal thiol groups that form a central disulfide linkage. The disulfide functions as a hydrophobic swivel in the center of the membrane. These compounds have the general formula X—(CH$_2$)$_m$SS(CH$_2$)$_n$—Y in which m is 0 or an integer from 1 to about 32, n is 33-m, and X and Y are first and second fluorophores, respectively.

As would be readily appreciated by those skilled in the art, the linker groups may be reacted with appropriately substituted or functionalized first and second fluorophores using conventional coupling chemistries. Further, it is obvious that the linker group may be attached to a fluorophore at a variety of different positions. Important locations ("X") for attachment of the linker in exemplary classes of oxonols are illustrated below; R indicates the location of side chains (as hereinbefore defined).

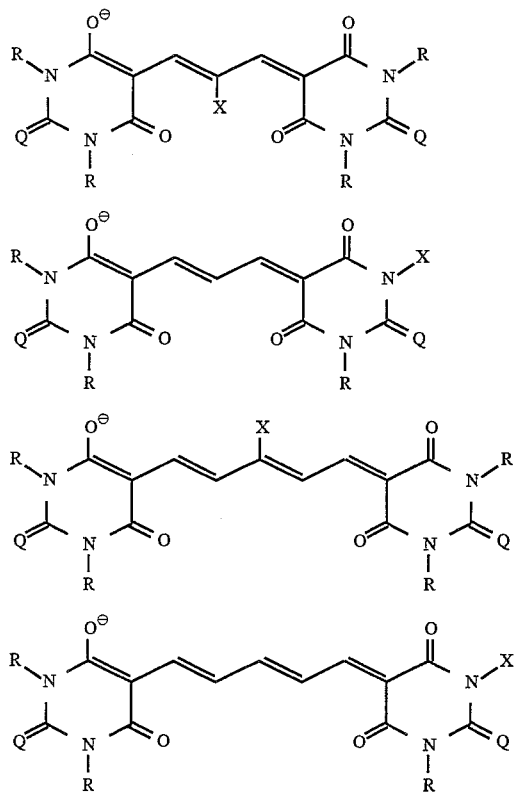

Single cells were used in the examples so that the optical signals could be compared with voltage changes accurately known from traditional microelectrode techniques, such as patch clamping, which are applicable only to single cells. Once the responsivity of the dyes is demonstrated and calibrated, the dyes may be used for many applications in which microelectrodes are not applicable. Indicators can either resolve the different electrical potentials of many neighboring cells or neighboring parts of a single cell, or give an average reading for all the membrane locations, depending on whether the optical signal is spatially imaged or pooled. Conventional techniques only read the potential at the tip of an electrode. Therefore, indicators are particularly advantageous for monitoring the membrane potential of many neurons or muscle cells simultaneously. Optical indicators, unlike conventional microelectrodes, do not require physical puncture of the membrane; in many cells or organelles, such puncture is highly injurious or mechanically difficult to accomplish. Indicators are thus the only technique suitable for cells too small or fragile to be impaled by electrodes. Indicators can read the local electric field in the interior of the membrane, which is the physical parameter that actually influences membrane proteins; electrodes monitor the overall potential between the two aqueous phases, which includes not only the interior electric field but also the surface potentials on each side of the bilayer. If the two surface potentials are variable or do not cancel each other out, the potential measured by electrodes will not accurately reflect the important electric field across the membrane interior.

The invention may be better understood with reference to the accompanying examples, which are intended for purposes of illustration only and should not be construed as in any sense limiting the scope of the invention as defined in the claims appended hereto.

EXAMPLES

Example 1

All starting materials and reagents were of the highest purity available (Aldrich; Milwaukee, Wis.) and used without further purification, except where noted. Solvents were HPLC grade (Fisher) and were dried over activated molecular sieves 3 Å. NMR spectra were acquired on a Varian Gemini 200 MHz spectrometer (Palo Alto, Calif.). The spectra were referenced relative to the residual solvent peak (CHCl$_3$, δ=7.24 ppm). Fluorescence spectra were taken on a SPEX Fluorolog-2 (Edison, N.J.) and were corrected for lamp and detector wavelength variations using the manufacturer supplied correction files.

DiSBA-C$_4$-(3) was synthesized based on the procedure for the ethyl derivative [British Patent 1,231,884]. 1,3-di-butyl-thiobarbiturate (500 mg, 2 mmol) was dissolved in 700 μL of pyridine. To this solution, a mixture of 181 μL (1.1 mmol) of malonaldehyde bis(dimethyl acetal) and 100 μL of 1M HCl was added. The solution immediately turned red. After 3 h, half of the reaction mixture was removed and 2 equiv. of the protected malonaldehyde was added every hour for 4 h to the remaining mixture. The reaction mixture was then filtered to collect purple/black crystals of the DiSBA-C$_4$-(3) pyridinium salt. After washing the crystals with water and then drying under vacuum (0.5 torr), 67.2 mg of pure product was collected. $^1$H NMR (CDCl$_3$):δ8.91 (2H, d, J=5.1 Hz, py), 8.76 (1H, t, J=13.7 Hz, central methine), 8.52 (1H, t, J=8.0 Hz, py), 8.16 (2H, d, J=13.9 Hz, methine), 8.00 (2H, dd, J$_1$-J$_2$=6.9 Hz, py), 4.47 (8H, cm, NC$\underline{H}_2$CH$_2$CH$_2$CH$_3$), 1.69 (8H, cm, NCH$_2$C$\underline{H}_2$CH$_2$CH$_3$), 1.39 (8H, cm, NCH$_2$CH$_2$C$\underline{H}_2$CH$_3$), 0.95 (12H, t, J=6.4 Hz, methyl).

To prepare 1,3-di-butyl-thiobarbiturate, 1.22 g of Na (53 mmol) was slowly dissolved in 20 mL of dry ethanol under argon. To the ethoxide solution, 8.5 g (8 mL, 53 mmol) of diethyl malonate followed by 5 g (26.5 mmol) of dibutylthiourea were added. The reaction mixture was heated and refluxed for 3 days. After cooling, the mixture was filtered. The filtrate was clarified with addition of water. Concentrated HCl was then added until the pH was 1–2. The acidic filtrate was then extracted 3× with hexanes. The extract was concentrated and 5.5 g of crude product precipitated out of solution. The solid was recrystallized from methanol with addition of small amounts of water yielding 4.23 g of the pure barbituric acid (65%). $^1$H NMR (CDCl$_3$): δ4.33 (4H, cm, NC$\underline{H}_2$CH$_2$CH$_2$ Ch$_3$), 3.71 (2H, s, ring CH$_2$), 1.63 (4H, cm NCH$_2$C$\underline{H}_2$CH$_2$CH$_3$), 1.35 (4H, cm, NCH$_2$CH$_2$C$\underline{H}_2$CH$_3$), 0.94 (6H, t, J=6.2 Hz, methyl).

Other oxonols were made using the same procedure, starting with the appropriate thiourea prepared from requisite primary amine and carbon disulfide [Bortnick, N., Luskin, L. S., Hurwitz, M. D., and Rytina, A. W. 1956. t-Carbinamines.RR'R"CNH$_2$. III. The preparation of isocyanates, isothiocyanates and related compounds. *J. Am. Chem. Soc.* 78:4358–4361]. An exemplary synthesis of DiSBAC$_6$(3) is depicted below.

fluorescence changes due to redistribution of the dyes into the cell were observed during depolarizations greater than 1 s. The cardiac myocytes [Henderson, S. A., Spencer, M., Sen, A., Kumar, C., Siddiqui, M. A. Q., and Chien, K. R. 1989. Structure organization, and expression of the rat cardiac myosin light chain-2 gene. *J. Biol. Chem.* 264:18142–18146] were a gift of Professor Kennneth Chien, UCSD. The Jurkat lymphocyte suspensions were grown in

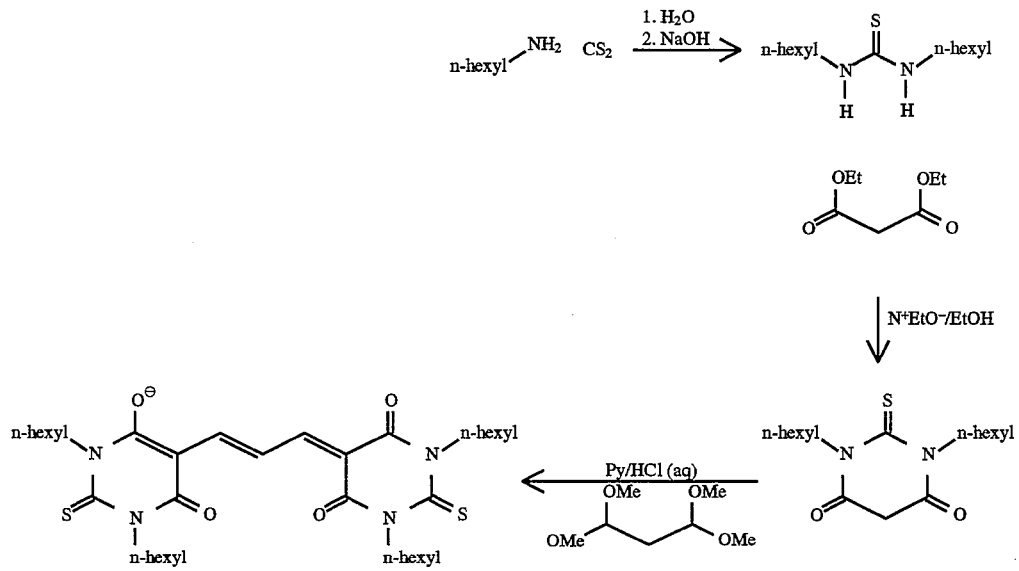

FL-WGA was purchased from Sigma Chemical Co. (St. Louis, Mo.). TR-WGA was prepared from WGA and Texas Red (Molecular Probes; Eugene, OR) in a 100 mM bicine buffer at pH 8.5. A 73 µM soltition of WGA was reacted with a 6-fold excess of Texas Red for 1 h at room temperature. The protein conjugate was purified on a G-25 sephadex column.

All cells were grown and handled like L-M(TK$^-$) except where noted. L-M(TK$^-$) cells were grown in Dulbecco's Modified Eagle Media (Gibco; Grand Island, N.Y.) with 10% fetal bovine serum (FBS) and 1% penicillin streptomycin (PS) (Gemini; Calabasas, Calif.). B104 cells were differentiated with 1 µM retinoic acid for 5 days prior to use. The cells were plated on glass coverslips at least one day before use. The adherent cells were washed and maintained in 2.5–3.0 mL of HBSS with 1 g/L glucose and 20 mM HEPES at pH 7.4. A freshly prepared 75 µM aqueous solution of the appropriate oxonol was made prior to an experiment from a DMSO stock solution. The cells were stained by mixing 100 µL of the oxonol solution with 750 µL of the bath and then adding the diluted solution to the cells. The dye was left for 30–40 minutes at a bath concentration of 2.3 µM. 1.5 mM β-cyclodextrin in the bath solution was necessary for cell loading of DiSBA-C$_6$-(3). The butyl and ethyl derivatives were water-soluble enough to load cells with out β-cyclodextrin complexation. DiSBA-C$_{10}$-(3) was loaded in a pH 7.4 solution containing 290 mM sucrose and 10 mM HEPES, 364 mOsm, for 10 min at a bath concentration of 10 µM. DiSBA-C$_{10}$-(3) labeling was quenched by replacing the bath with HBSS solution. The cells were stained with 15 µg/mL of FL-WGA for 15 minutes. The B104 cells required a 125 µg/mL bath concentration to give satisfactory lectin staining. The excess dyes were removed with repeated washes with HBSS. If the excess ethyl or butyl oxonol derivatives were left in the bath, slow currents and RPMI media with 5% heat inactivated FBS and 1% PS. 15–20 mL aliquots of the cellular suspension were washed three times before and after dye staining by centrifugation at 100×g for 4 minutes followed by additions of fresh HBSS.

The fluorescently labeled cells were excited with light from a 75 W xenon lamp passed through 450–490 nm excitation interference filters. The light was reflected onto the sample using a 505 nm dichroic. The emitted light was collected with a 63× Zeiss (1.25 or 1.4 numerical aperture) lens, passed through a 505 nm long pass filter and directed to a G-1B 550 nm dichroic (Omega; Brattleboro, Vt.). The reflected light from this second dichroic was passed through a 515 DF35 bandpass filter and made up the FL-WGA signal. The transmitted light was passed through a 560 or 570 LP filter and comprised the oxonol signal. For experiments using the oxonol as a donor to TR-WGA, the 550 nm dichroic was used for excitation and a 580 nm dichroic was used to split the emission. The long wavelength Texas Red fluorescence was passed through a 605 nm DF55 bandpass filter. Voltage dependent fluorescence changes in single cells were measured using a Nikon microscope attached to a Photoscan II photometer equipped with two R928 PMTs for dual emission recordings. A 7-point Savitsky-Golay smoothing routine was applied to all optical data [Savitsky, A. and Golay, M. J. E. 1964. Smoothing and differentiation of data by simplified least squares procedure. *Anal. Chem.* 36:1627–1639], unless otherwise noted. The 1–2 KHz single wavelength data was acquired with an Axobasic program that used the TTL pulse counting routine LEVOKE. The confocal image was acquired using a home built high speed confocal microscope [Tsien, R. Y. and B. J. Bacskai. 1994. Video-rate confocal microscopy. In Handbook of Biological Confocal Microscopy. J. B. Pawley, editor. Plenum Press, New York]. The cell was voltage-clamped at a holding potential of −70 mV. After a 200 ms delay, the cell was given a 200 ms depolarizing square voltage pulse to 50 mV. Images were collected every 67 ms. The second and fifth images are shown in the figure and are the average of 16 images.

Patch clamp recording were made using an Axopatch 1-D amplifier equipped with a CV-4 headstage from Axon Instruments (Foster City, Calif.). The data were digitized and stored using the PCLAMP software. The pH 7.4 intracellular solution used contained 125 mM potassium gluconate, 1 mM $CaCl_2.2H_2O$, 2 mM $MgCl_2.6H_2O$, 11 mM EGTA, and 10 mM HEPES. For the B104 cells, 4 mM ATP and 0.5 mM GTP were added.

The quantum yield of DiSBA-$C_6$-(3) was determined relative to rhodamine B in ethanol ($\Phi_F$=0.97) [Weber, G. and Teale, F. W. K. 1957. Determination of the absolute quantum yield of fluorescent solutions. *Faraday Soc. Trans.* 53:646–655]. $R_o$ was calculated following standard procedures [Wu, P. and Brand, L. 1994. Resonance energy transfer: methods and applications. *Anal. Biochem.* 218:1–13]. The spectra of FL-WGA in HBSS and DiSBA-$C_6$-(3) in octanol were used to determine the overlap integral. Values of 1.4 and 0.67 were used for the index of refraction and orientation factor respectively.

Figure 2:
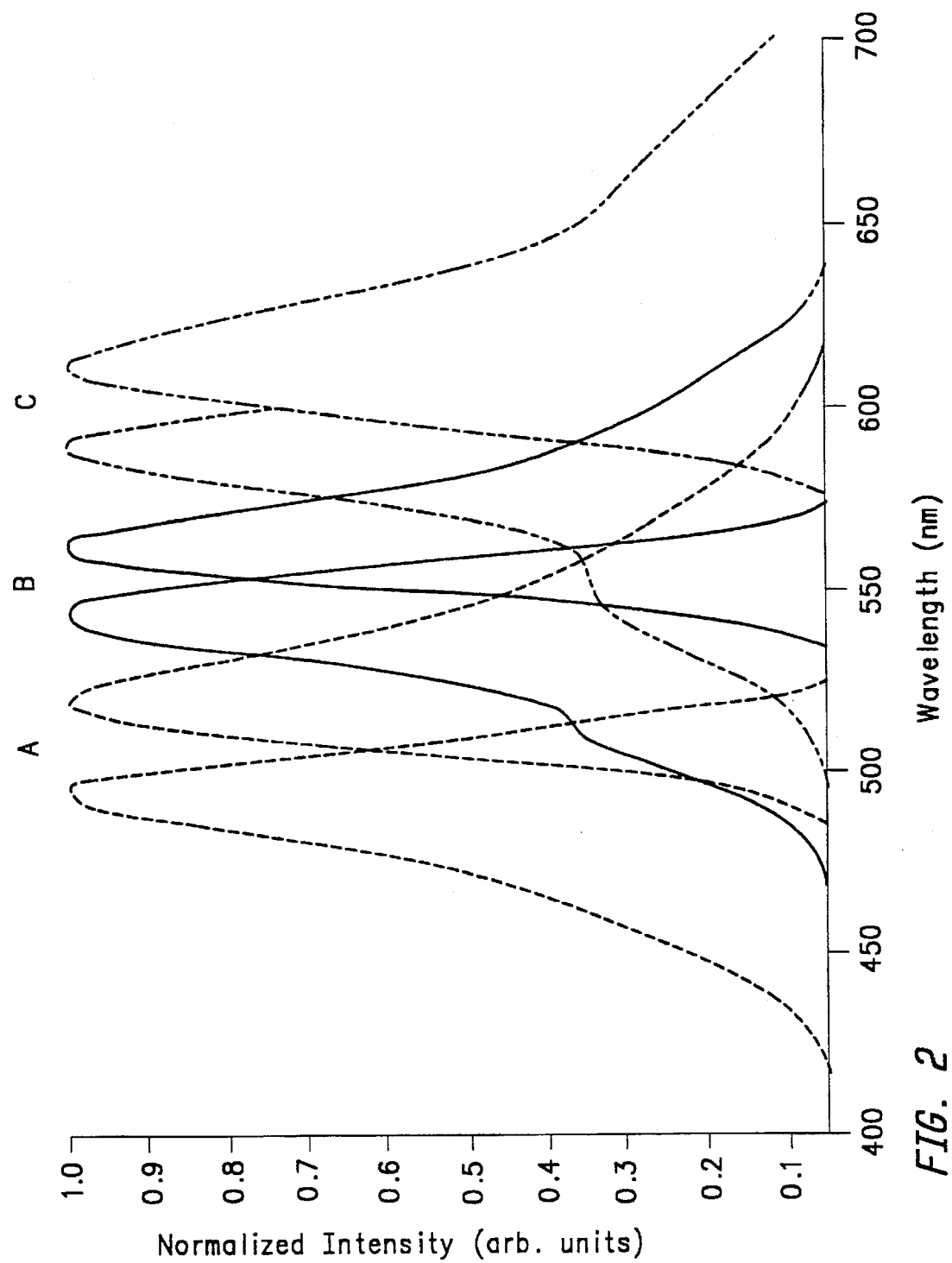
FIG. 2 illustrates normalized excitation and emission spectra for (A) FL-WGA in HBSS (-----), (B) (1,3-dihexyl-2-thiobarbiturate)trimethine oxonol [DiSBA-$C_6$-(3)] in octanol (——), and (C) TR-WGA in HBSS (——)

Symmetrical bis(thiobarbiturate)oxonols were chosen as likely candidates for rapidly translocating fluorescent ions based on the above design criteria. The strong absorbance maximum ($\epsilon$~200,000 $M^{-1}cm^{-1}$) at 540 nm and good quantum yield (0.40) in membranes makes them desirable for use as a fluorescence donors or acceptors in cells. The fluorescence excitation and emission spectra of DiSBA-$C_6$-(3) is shown in FIG. 2 those for FL-WGA and TR-WGA. The excitation spectra are the shorter of each pair. Octanol was selected as the oxonol solvent in order to mimic the membrane environment.

Another extremely useful property of these oxonols is that their fluorescence emission maximum at 560 nm is 20 times brighter when bound to membranes than in aqueous solution [Rink, T. J., Montecucco, C., Hesketh, T. R., and Tsien, R. Y. 1980. Lymphocyte membrane potential assessed with fluorescent probes. *Biochim. Biophys. Acta* 595:15–30]. Furthermore, the negative charge is delocalized throughout the chromophore with the four equivalent oxygens containing the majority of the charge. The high electron affinity of the thiobarbiturate moieties discourages protonation, pKa <1, and resists photooxidative bleaching. The four N-alkyl groups and the thiocarbonyl give the molecule a necessary amount of hydrophobicity needed for tight membrane binding and rapid translocation. The translocation rates were studied in L-M(TK$^-$) cells using whole-cell voltage clamp recording. The L-M(TK$^-$) cells were chosen because they have very low background currents and are easy to patch clamp. These cells have a resting potential of –5 mV and no obvious voltage activated currents.

Figure 3:
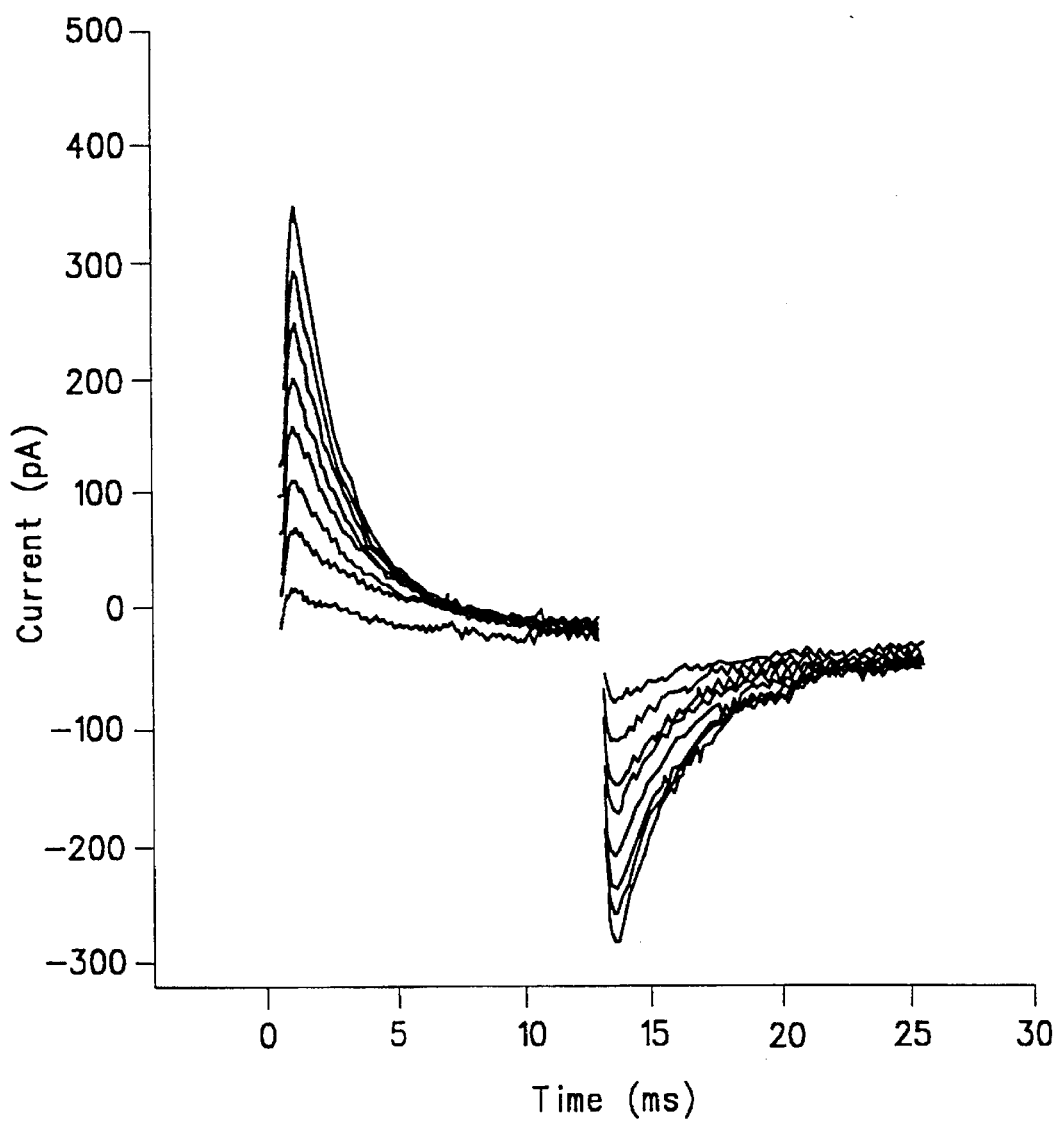
FIG. 3 illustrates displacement currents of 2.3 µM DiSBA-$C_6$-(3) in L-M(TK$^-$) cells at 20° C.

Displacement currents from DiSBA-$C_6$-(3) at 20° C. are displayed in FIG. 3. 12.5 ms long voltage steps at 15 mV increments were applied to the cell, from a holding potential of –70 mV. The larger, faster transients due to simple membrane capacitance transient could be minimized using the capacitance and series resistance compensation capabilities of the Axopatch amplifier, allowing the displacement currents to be clearly observed. The currents are due to redistribution of the membrane-bound oxonol in response to 8 alepolarizations. The time constant for the displacement current is 2 ms for 120 mV depolarization. Equal amounts of charge move at the onset and conclusion of the voltage step, but in opposite directions, consistent with redistribution of stored ions from one energy minimum to the other across the plasma membrane. Furthermore, the induced capacitance dq/dV from the oxonol movement is calculated to be ~5 pF for 100 mV alepolarization. This value corresponds to roughly one third the membrane capacitance without the dye. Interestingly, sodium channel gating charges are also responsible for about 33% of the total capacitance of squid axons for small alepolarizations [Hodgkin, A. 1975. The optimum density of sodium channels in an unmyelinated nerve. *Philos. Trans. R. Soc. Lond.* [Biol] 270:297–300]. Negligible currents were observed in the absence of the oxonol. DiSBA-$C_{10}$-(3) gave displacement currents of approximately the same speed, whereas analogues with R=butyl and ethyl gave much slower currents. The butyl compound had a time constant of ~18 ms and the currents from the ethyl compound were very small, slow, and difficult to observe.

Figure 4:
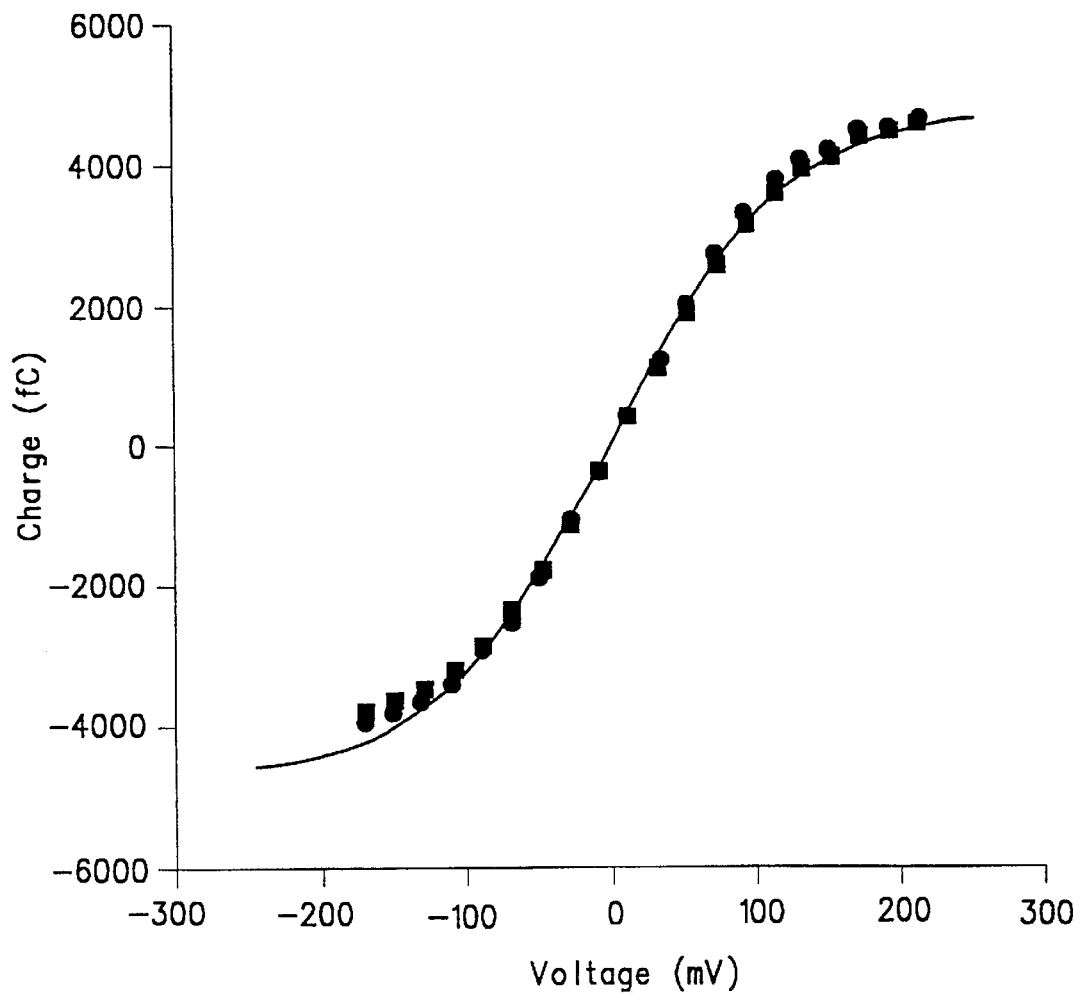
FIG. 4 illustrates voltage dependence of DiSBA-$C_6$-(3) moved during the displacement and tailcurrents for voltage changes from a −30 mV holding potential.

FIGS. 4 and 5 show the voltage dependence and time constants for charge translocation in a cell loaded with about 4 times as much oxonol as in the experiment of FIG. 3. In FIG. 4, the circles are the data from the on response and the squares from the tail currents. The raw data were fit to a single exponential and the charge moved, the area, was calculated as the product of the current amplitude and the time constant. The experimental data are in reasonable accord with existing models of hydrophobic ion transport between two energy minima near the aqueous interfaces of the lipid bilayer [Ketterer, B., Neumcke, B., and Läuger, P. 1971. Transport mechanism of hydrophobic ions through lipid bilayer membranes. *J. Membrane Biol.* 5:225–245; Andersen, O. S. and Fuchs, M. 1975. Potential energy barriers to ion transport within lipid bilayer. *Biophys. J.* 15:795–830; Benz, R., Läuger, P., and Janko, K. 1976. Transport kinetics of hydrophobic ions in lipid bilayer membranes. *Biochim. Biophys. Acta* 455:701–720]. These models predict that the equilibrium charge displacement $\Delta q(V)$ and the translocation time constant $\tau(V)$ should depend on the externally applied membrane potential V in the following manner:

$$\Delta q(V) = \Delta q_{max} \tanh\left[\frac{q\beta(V - V_h)}{2kT}\right] \quad (1)$$

$$\tau(V) = \tau_{max} \text{sech}\left[\frac{q\beta(V - V_h)}{2kT}\right] \quad (2)$$

$V_h$, the membrane potential at which there are equal numbers of ions in each potential energy well, could differ from zero because of membrane asymmetry. $\beta$ is the fraction of the externally applied potential effectively felt by the translocating ion; q is the charge on each ion, k and T are Boltzmann's constant and absolute temperature. $\Delta q_{max}$ and $\tau_{max}$ are respectively the total charge in each energy well and the time constant for translocation, both at $V=V_h$. The smooth curve in FIG. 4 is the fit to Eq. 1 with $\Delta q_{max}$= 4770±140 fC, $\beta$=0.42±0.02, and $V_h$=–3.8±1.5 mV. Likewise the smooth curve in FIG. 5 is the fit to Eq. 2 with $\tau_{max}$=2.9 ms at $V_h$=–5 mV and $\mu$=0.42.

These results demonstrate that the oxonol senses a significant part of the electric field across the membrane, that it translocates in ~3 ms or less, and that the greatest sensitivity and linearity of translocation as a function of membrane potential is in the physiologically relevant range.

To transduce charge displacements into optical signals, the oxonol fluorescences at the intracellular and extracellular membrane binding sites must be made different. Fluorescence asymmetry is created with the introduction of fluorescently labeled lectins bound to the extracellular membrane surface. Excitation of FL-WGA leads to energy transfer to oxonols located in the extracellular membrane binding site as shown in FIG. 1. The extinction coefficient and the fluorescence quantum yield of FL-WGA were measured to be 222,000 $M^{-1}cm^{-1}$ (~3 fluorescein/protein) and 0.23, respectively. In Jurkat cell suspensions labeled with FL-WGA, up to 30% of the lectin fluorescence intensity was quenched upon titration of DiSBA-$C_4$-(3). In the best case where all of the quenching is due to energy transfer, the average distance from the lectin to the membrane-bound oxonol is still greater than 50 Å, the calculated Förster distance $R_o$ for the FL-WGA/oxonol (FLOX) pair. The spectral overlap between the FL-WGA emission and DiSBA-$C_6$(3) excitation is given in FIG. 2. Because FRET falls off with the inverse sixth power of the distance separating the two fluorophores, energy transfer to oxonols in the intracellular membrane site, an additional 40 Å away, is probably negligible.

Figure 6:
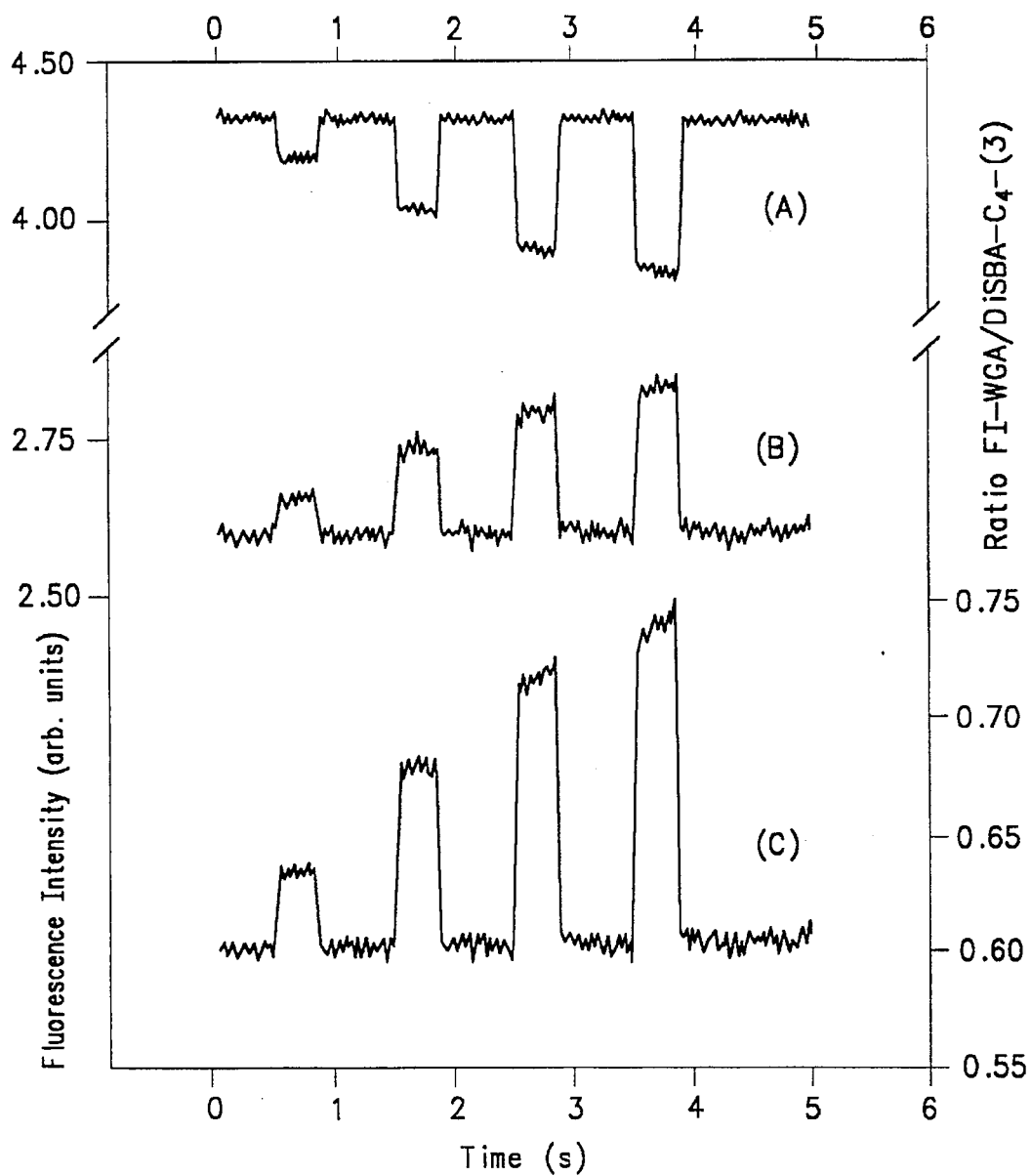
FIG. 6 illustrates simultaneous fluorescence changes of FLOX2 in response to 4 depolarizations from −70 mV of 40, 80, 120, and 160 mV in a L-M(TK) cell at 20° C., with the single wavelength fluorescence emission traces of DiSBA-$C_4$-(3) and FL-WGA being shown in panels A and B, respectively, and the FL-WGA/DiSBA-$C_4$-(3) ratio displayed in (C)

Upon alepolarization, the oxonol molecules redistribute such that more are bound to the intracellular site and less to the extracellular one. This change manifests itself with a decrease in the energy transfer, resulting in an increase in the fluorescence of the FL-WGA and a concomitant decrease in the oxonol emission. The fluorescence signals in a voltage clamped L-M(TK$^-$) cell labeled with FLOX2 (the DiSBA-$C_4$-(3)/FL-WGA pair) and depolarized with four increasing voltage steps are shown in FIG. 6. The data are the average of 29 sweeps. The FL-WGA emission increases 7–8%, the oxonol fluorescence decreases 10% and the FL-WGA/oxonol emission ratio changes 19% for a 120 mV depolarization. The simultaneous changes in donor and acceptor emissions is consistent with the FRET mechanism outlined in FIG. 1. The decrease in oxonol emission with depolarization is opposite to what is observed for the slow voltage-sensitive uptake of oxonols in cells [Rink et al. 1980, sttpra]. The fluorescence changes have time constants of ~18 ms 20° C., in agreement with the DiSBA-$C_4$-(3) displacement currents. No large fluorescence changes are observed in the absence of FL-WGA. The translocation rate of DiSBA-$C_4$-(3) speeds up with increasing temperature. The time constant falls to 7–8 ms at 29° C., corresponding to an activation energy of ~17 kcal/mol. However, raising the temperature also increases internalization of the lectin and eventually decreases the fluorescence change. The oxonols with R=ethyl and butyl also reach internal cellular membranes, though active membrane internalization is probably not necessary. Additional dilution of the voltage-dependent FRET signals arises from spectral overlap of the fluorescein and oxonol, such that some of the light in the fluorescein emission channel comes from the oxonol and vice versa.

Figure 7:
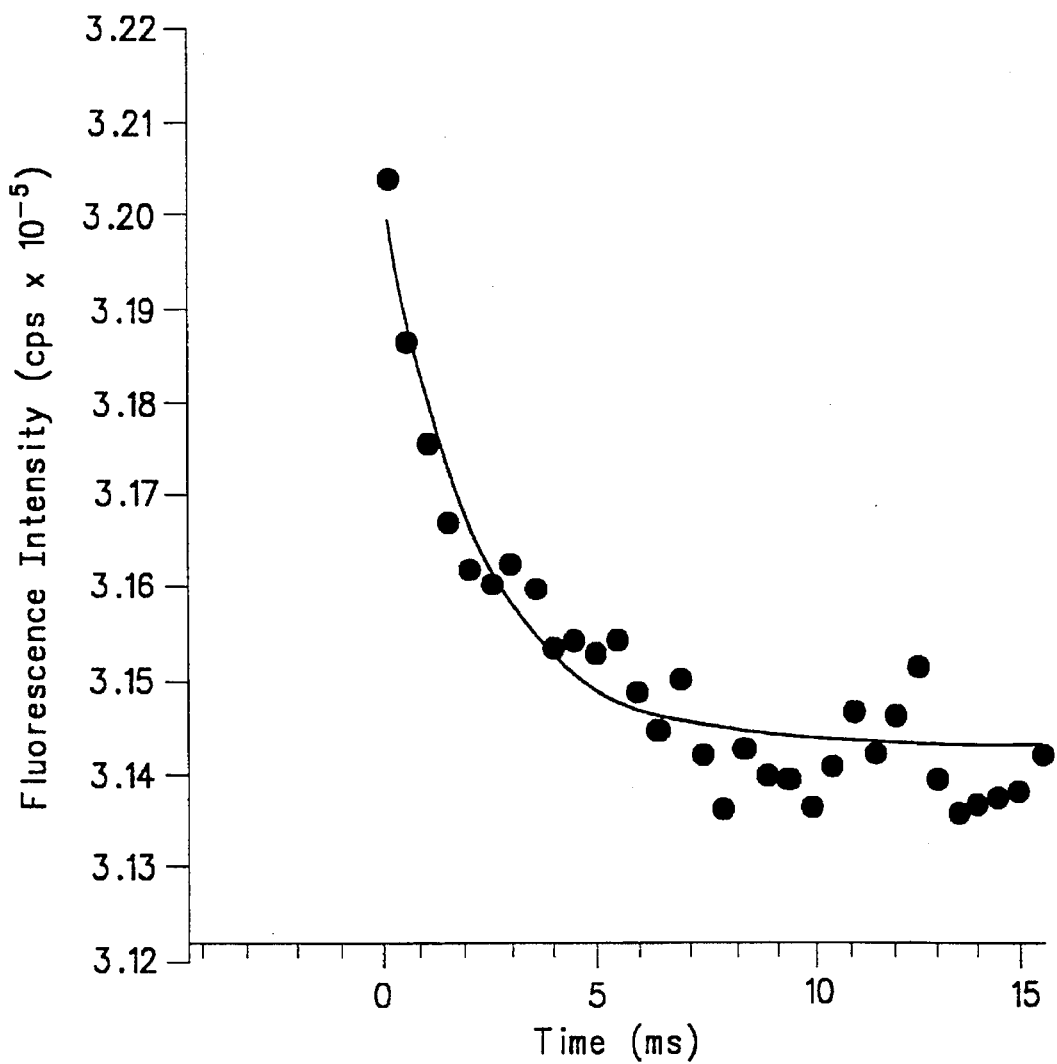
FIG. 7 illustrates the time course of the fluorescence change of (B) DiSBA-$C_{10}$-(3) from FLOX5 in response to a 100 mV depolarization from −70 mV.

Increasing the length of the alkyl chains on the oxonol improves the response times significantly. The DiSBA-$C_6$-(3)/FL-WGA pair, FLOX4, has a time constant of ~3 ms at 20° C., while the DiSBA-$C_{10}$-(3)/FL-WGA pair, FLOX5, responds with a time constant of 2 ms, as shown in FIG. 7. The solid curve is a fit to a single exponential with a 2 ms time constant. The data is the average of 3 L-M(TK$^-$) cells, at 20° C., acquired at 2 kHz. The response in the figure is slightly slower than the true value because of smoothing. The fluorescence time constants are in agreement with those from the displacement currents, for example in FIG. 3. The beneficial effect of adding hydrophobicity to the oxonol in the form of longer alkyl chains reaches a plateau. There is a large 6-fold increase in translocation rate substituting hexyl for butyl on the oxonol core. However, addition of twice as many methylene groups in going from the hexyl to the decyl compound results in less than a 2-fold increase. These faster translocating oxonols are essentially insoluble in water and require modified procedures to load into cells. DiSBA-$C_6$-(3) is easily loaded in normal medium supplemented with 1.5 mM β-cyclodextrin to complex the alkyl chains. Non-fluorescent DiSBA-$C_6$-(3) aggregates in Hanks Balanced Salt Solution (HBSS) become fluorescent upon addition of β-cyclodextrin. DiSBA-$C_{10}$-(3) requires loading in a medium of low ionic strength with osmolarity maintained with sucrose. Labeling is confined almost exclusively to the plasma membrane, presumably because the hydrophobicity is now great enough to prevent desorption from the first membrane the dye encounters.

The direction of energy transfer can be reversed using TR-WGA instead of FL-WGA. DiSBA-$C_6$-(3) functions as a FRET donor to TR-WGA in L-M(TK$^-$) cells with the same response time as FLOX4. The spectral overlap of this FRET pair is shown in FIG. 2. The signal change, however, is only one half that for FLOX4. The limiting factor at present seems to be that the surface binding sites for the lectin are not dense enough on these cells for the TR-WGA to capture a large fraction of the donor excitation.

Figure 8:
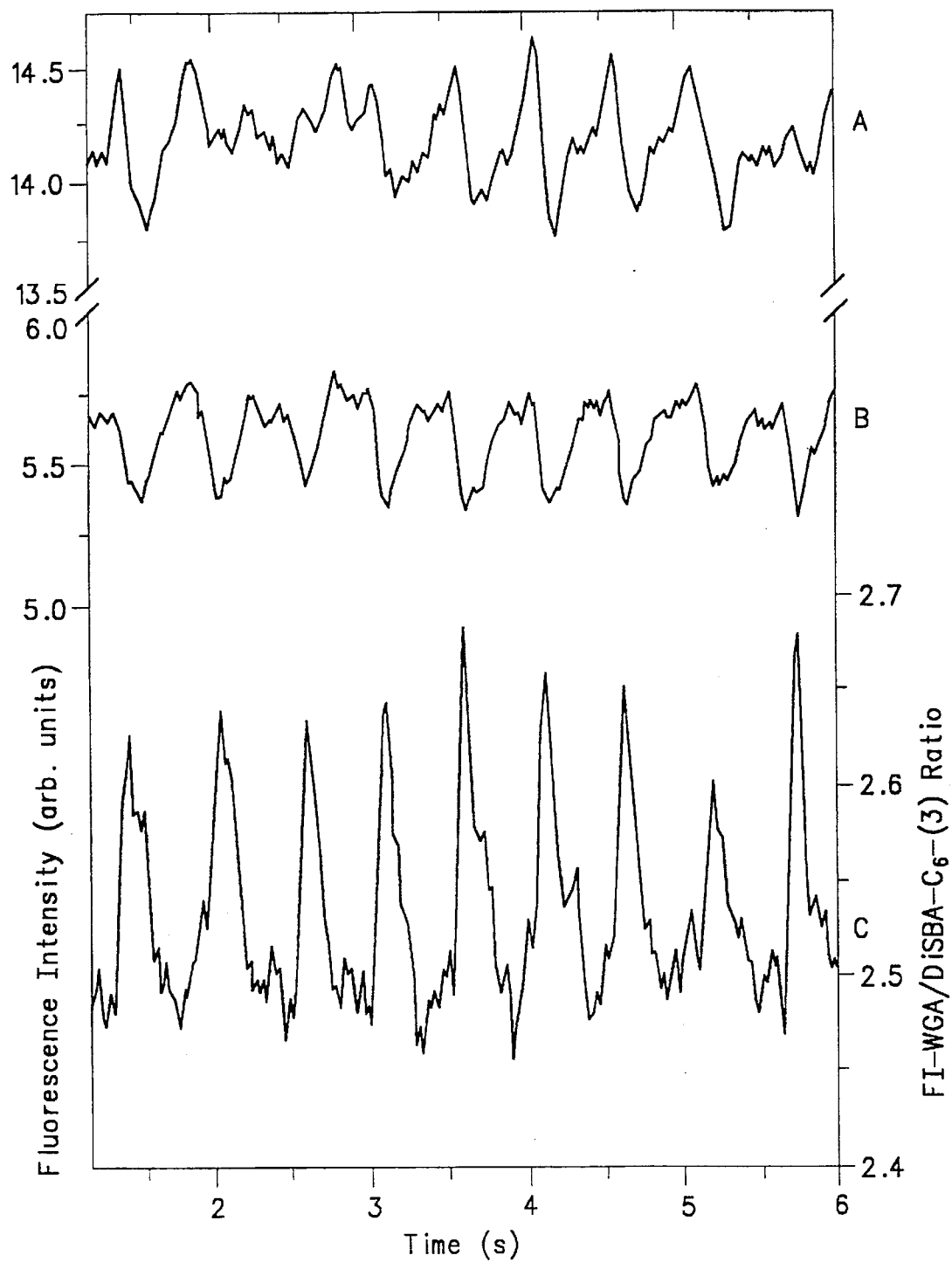
FIG. 8 illustrates a single sweep trace of FLOX4 fluorescence ratio changes in beating neonatal cardiac myocytes, with the top trade (A) showing the FL-WGA channel, (B) the longer wavelength oxonol channel and (C) the FL-WGA/oxonol ratio, in which motion artifacts are significantly reduced.

The FLOX4 system was tested in a variety of cell lines. In neonatal cardiac myocytes, the two fluorophores could be loaded without affecting the spontaneous beating. Therefore, the added capacitance from the oxonol displacement current did not prevent generation of action potentials. The periodic 90 mV action potentials [Conforti, L., Tohse, N., and Sperelakis, N. 1991. Influence of sympathetic innervation on the membrane electrical properties of neonatal rat cardiomyocytes in culture. *J. Devel. Physiol.* 15:237–246] could be observed in a single sweep, FIG. 8C. The ratio change without subtraction of any background fluorescence was 4–8%. Motion artifacts were observed in the single wavelength data. In FIGS. 8A and B, large slow changes in the detected light were observed in both channels. Satisfyingly, these effects were essentially eliminated in the ratio data. The data were acquired at 100 Hz and 10 µM of isoproterenol was added to the bath solution. The voltage dependent fluorescence changes are faster than the mechanically based artifacts, as expected [Hill, B. C. and Courthey, K. R. 1982. Voltage-sensitive dyes discerning contraction and electrical signals in myocardium. *Biophys. J.* 40:255–257]. Some cells, loaded with oxonol at 2.3 µM, did stop beating after about 7 seconds of continuous exposure to the xenon arc illumination. At 0.6 µM loading, the phototoxicity and unfortunately the signal were reduced. In differentiated B104 neuroblastoma cells an 8% ratio increase was recorded, without any background subtraction, for a 120 mV depolarization. The inward sodium currents did not deteriorate from phototoxic effects during experiments with excitation exposures totaling 10–20 s. FLOX4 labeled 1321N astrocytoma cells showed oxonol and FL-WGA fluorescence almost exclusively on the plasma membrane.

Figure 9:
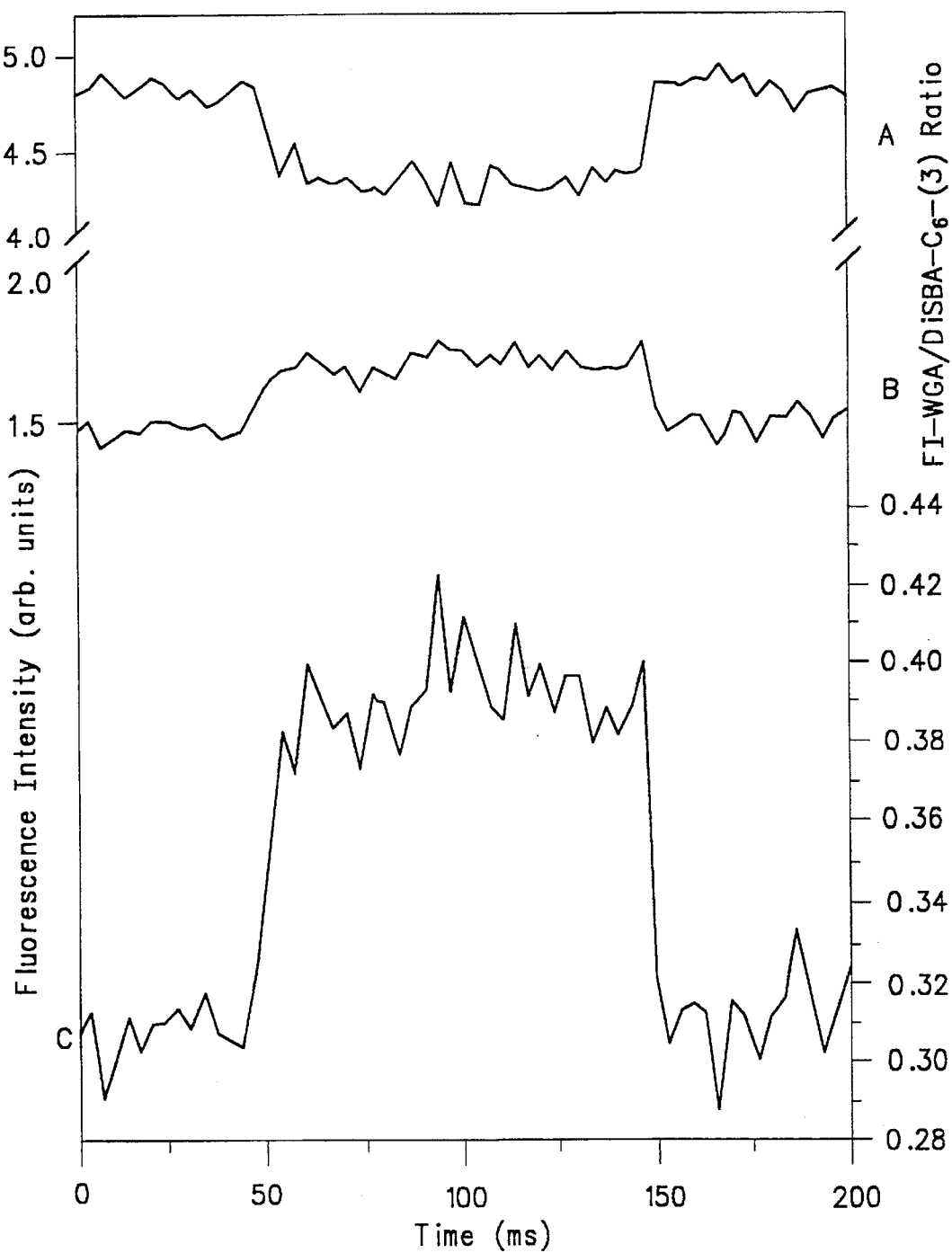
FIG. 9 illustrates the fluorescence changes of FLOX4 in a voltage clamped astrocytoma cell, the top trace (A) being the DiSBA-$C_6$-(3) emission, (B) the FL-WGA fluorescence signal and (C) the FL-WGA/oxonol ratio.

Ratio changes of 22–34% for 100 mV were observed in photometry experiments such as FIG. 9. After a 50 ms delay, the membrane potential was depolarized 100 mV from –70 mV for 100 ms. The traces are the average of 4 sweeps acquired at 300 Hz, with no smoothing. The time constant for the fluorescence changes is less than 3.3 ms consistent with the displacement currents, such as those in FIG. 3. A small background signal was subtracted from the starting signal, <5% for the oxonol channel and <15% for the fluorescein channel. The fluorescence intensities in the fluorescein and oxonol channels increased ~17% and decreased ~16% respectively for 100 mV depolarization. In these cells, unlike the L-M(TK$^-$), the crosstalk between emission channels was decreased and larger changes occurred in the fluorescein signal. These signal changes are the largest millisecond membrane potential dependent ratio changes observed in single cells. Previous investigations have shown that 4-ANEPPS gives a 9% /100 mV excitation ratio change [Montana, V., Farkas, D. L., and Loew, L. M. 1989. Dual-wavelength ratiometric fluorescence measurements of membrane potential. *Biochemistry* 28:4536–4539]. In addition, FLOX4's fluorescence changes in each emission channel is comparable to the largest reported changes, for example, the 21% /100 mV change in a neuroblastoma using RH-421 [Grinvald, A., Fine, A., Farber, I. C., and Hildesheim, R. 1983. Fluorescence monitoring of electrical responses from small neurons and their processes. *Biophys. J.* 42:195–198]. The large FLOX4 signals made it possible to record images of voltage clamped L-M(TK⁻) and astrocytoma cells using a high speed confocal microscope.

The astrocytoma cells gave a 10–20% ratio increase that was localized to the plasma membrane for a 120 mV depolarization.

Example 2

In a 25 mL flame dried two neck flask 0.788 g (580 μL, 2.2 mmol) of compound I was dissolved in 6 mL of dry hexane under argon. After cooling the flask to −70° C, 1.46 mL of a 1.5M n-butyllithium solution (2.2 mmol) was added via syringe. In a separate flask 0.60 dry borane II was dissolved in a deoxygenated mixture of 6 mL hexane and 1.5 mL of freshly distilled THF. The borane solution was then added via syringe to the lithium reagent. A solid immediately precipitated. After 30 min the cold bath was removed and the reaction was allowed to slowly heat up. Three hours later the solvent was decanted off and the solid rinsed with more hexane. The solid was dissolved in acetonitrile and water and then poured into a separatory funnel. The aqueous layer was again washed with hexane and then extracted with ethyl acetate. Half of the extract was concentrated yielding 124.9 mg( 170.5 μmol) of the desired product. This product was then mixed with 97 mg of tetrabutylammonium fluoride in acetonitrile for 15 min at room temperature. After workup 129.1 mg of compound III as the tetrabutylamnionium salt was recovered (93 %). $^1$HNMR (d$_6$ acetone) δ 7.61 (br d, 2H, CF$_3$-phenyl group), 7.43 (cm, ~3H, CF$_3$-phenyl group), 6.90–7.26 (cm, ~7H, CF$_3$-phenyl group), 3.43 (cm, 8H, NC H$_2$CH$_2$CH$_2$CH$_3$), 1.81 (cm, ~8H, NCH$_2$CH$_2$CH$_2$CH$_3$), 1.42 (cm, ~8H, NCH$_2$CH$_2$CH$_2$ CH$_3$), 0.93 (t, J=7.1 Hz, NCH$_2$CH$_2$CH$_2$CH$_3$).

For synthesis of compound IV, in a 5 mL round bottom flask 14 mg (17.2 umol) of compound III, 7 mg (25.8 umol) of bromomethylbimane, 27.3 mg (172 umol) of potassium carbonate, and 5 mg (18.9 umol) of 18-crown-6 were mixed in 0.6 mL of dry acetonitrile. The mixture was heated at 70° C. 1.5 h. After cooling, the reaction mixture was dissolved in ethyl acetate and washed 3× with water. The organic residue was purified by flash chromatography eluting with toluene/acetone (2:1). The major band was collected yielding 12.1 mg (70%) of pure product IV tetrabutyl ammonium salt. $^1$HNMR (d$_6$ acetone) δ 7.58 (br d, 2H, CF$_3$-phenyl group), 7.4–7.5 (cm, 2H, CF$_3$-phenyl group), 7.0–7.3 (cm, ~10H, CF$_3$-phenyl group), 5.29 (d, J=1.6 Hz, 2H, CH$_2$), 3.46 (cm, 8H, NCH$_2$CH$_2$CH$_2$CH$_3$), 2.56 (d, J=0.7 Hz, 3H, bimane methyl), 1.84 (cm, ~8H, NCH$_2$CH$_2$CH$_2$CH$_3$), 1.79 (d, J=0.8 Hz, 3H, bimane methyl), 1.76 (s, 3H, bimane methyl), 1.44 (cm, ~8H, NCH$_2$CH $_2$CH$_2$CH$_3$), 0.98 (t, J=7.2 Hz, NCH$_2$CH$_2$CH$_2$CH$_3$) Φ$_f$=0.73 in dioxane based on quinine sulfate in 0.1N H $_2$SO$_4$ Φ$_4$=0.55.

Example 3

This example illustrates the synthesis of asymmetric oxonols containing a built-in linker group. For synthesis of compound V, 4.35 g (21.7 mmol) of 1,12-diaminododecane was dissolved in 40 mL of dry CH$_2$Cl$_2$. Via syringe, 2.62 mL (2.17 mmol) of butyl isothiocyanate was added to the reaction flask. A white solid had precipitated after 15 minutes. One hour after the addition, the reaction mixture was filtered. The tiltrate was then evaporated leaving a white solid. The solid was redissolved in 45 mL of dry CH$_2$Cl$_2$ and mixed with 2.44 mL of N,N-diisopropylethylamine (DIEA) and 3.9 g (17.9 mmol) of di-tert-butyl dicarbonate. After reacting for 1 hour, the mixture was poured into a separatory funnel and washed with 5% sodium bicarbonate. A solid came out of solution and was filtered away (<100 mg). The organic solution was then washed with water and a saturated brine solution. The organic layer was then dried with MgSO$_4$ and filtered. The filtrate was evaporated leaving a white solid, which was recrystallized in isopropyl ether yielding 4.30 g (10.3 mmol) of pure compound V (48% overall). $^1$HNMR (CDCl$_3$) δ 5.73 (br s, 2H, thioamide), 4.50 (br s, 1H, carbamate), 3.40 (br s, 4H, NCH$_2$), 3.10 (q, J=7.2 Hz, ~3 H, CH$_2$ next to carbamate), 1.44 (s, 9H, t-butyl), 1.2–1.7 (cm, bulk CH$_2$), 0.94 (t, J=7.2 Hz, n-butyl methyl).

For preparing compound VI, 441 mg (19.2 mmol) of sodium was dissolved in 5 mL of dry ethanol under argon. When almost all of the sodium was dissolved, 2.92 mL (3.1 g, 19.2 mmol) of diethyl malonate was added to the ethoxide solution. Some solid precipitated out of solution. 4.0 g (9.6 mmol) of compound V was added and the mixture was refluxed under argon at 100° C. for 70 hours. After cooling, the reaction mixture was filtered and washed with ethanol. Water was added to the filtrate and a white solid precipitated out of solution. The solid (779 mg, mostly of unreacted starting material) was filtered away. The flitrate was then acidified to pH ~2 and then extracted into ethyl acetate. The organic layer was then dried with MgSO$_4$ and filtered. After removing the solvent, 1.6 g (3.3 mmol) of a yellow oil was recovered (34%). $^1$HNMR (CDCl$_3$) δ4.22 (cm, 4H, NCH$_2$ next to barbiturate), 3.63 (s, 2H, ring CH$_2$), 2.99 (cm, 2H, C H$_2$ next to carbamate), 1.53 (cm, 4H, NCH$_2$CH$_2$), 1.34 (s, 9H, t-butyl), 1.1–1.3 (cm, bulk CH$_2$s), 0.85 (t, J=7.4 Hz, n-butyl methyl).

To prepare compound VII, 1 mL of trifluoroacetic acid (TFA) was added with stirring to 200 mg (0.41 mmol) of compound VII dissolved in 3 mL of CH$_2$Cl$_2$. After 1.25 hours, all the solvent was removed under reduced pressure. One equivalent each of N-[5-(phenylamino)-2,4-pentadienylidene]aniline monohydrochloride and 1,3-di-n-butylthiobarbiturate was added and all three components dissolved in 1 mL pyridine and left overnight. The product was purified from the other pentamethine oxonols by flash chromatography. The nonpolar products were eluted with CHCl$_3$/CH$_3$OH (9:1). The pure product containing the linker eluted with CHCl$_3$/CH$_3$OH (1:1). The product was bound very tightly to the silica gel and only 10 mg of product was recovered. $^1$HNMR (CDCl$_3$/CD$_3$OD) δ 7.5–7.8 (cm, 4H, vinyl methines), 7.35 (t, J=~14 Hz, 1H, central methine), 4.34 (br t, ~10 H, NCH$_2$ next to barbiturate), 2.72 (cm, [18] 3H, CH$_2$ next to amine), 1.4–1.7 (br cm, ~12H, NCH$_2$CH$_2$), 1.0–1.4 (cm, ~40H, bulk CH$_2$s), 0.81 (t, J=7.3 Hz, 9H, n-butyl methyl).

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A composition of matter comprising:

a first reagant selected from the group consisting of membrane-bound hydrophobic fluorescent anions which redistribute from one face of the membrane to a second face in response to transmembrane potential; and a second reagant selected from the group consisting of fluorophores which undergo energy transfer with the firts reagant and quenchers of fluorescene of the first reagant, said secong reagant being located adjacent to either the one face or the second face of the membrane.

2. The composition according to claim 1, wherein the first and second raegants are bound together by a linker group.

3. A method of generating voltage-sensitive fluorescene changes in a system comprising a membrane, said method comprising:

introducing a first reagant selected from the group consisting of membrane-bound hydrophobic fluorescent anions which redistribute from one face of the membrane to a second face in response to transmembrane potential into the membrane;

introducing a second reagant selected from the group consisting of fluorophores which undergo energy transfer with the first reagant and quenchers of fluorescene of the first reagant, the second reagant being located adjacent to either the one face or the second face of the membrane; and observing a change in fluorescene when membrane potential is changed.

4. The method of claim 3, wherein the membrane is a plasma membrane of a biological cell.

5. The method of claim 3, wherein the first and second reagants are bound together by a linker group.

6. The method of claim 3, wherein:

the first reagent is independently selected from the group consisting of polymethine oxonols and tetra-aryl borates conjugated to a fluorophore; and the second reagant is independently selected from the group consisting of fluorescent lectins, xanthenes, cyanines, fluorescent phospholipids and fluorescent clclodextrins.

* * * * *

UNITED STATES PATENT AND TRADEMARK OFFICE
CERTIFICATE OF CORRECTION

PATENT NO. : 5,661,035
DATED : 08/26/97
INVENTOR(S) : Tsien et al.

It is certified that error appears in the above-identified patent and that said Letters Patent is hereby corrected as shown below:

In column 25, line 11, claim 1, replace "firts" with --first--; column 25, line 10, claim 1, replace "secong" with --second--; and column 25, line 14, claim 2, replace "raegants" with --reagants--.

In column 26, line 20, claim 6, replace "clclodextrins" with --cyclodextrins--.

Signed and Sealed this

Eighteenth Day of May, 1999

Attest:

Q. TODD DICKINSON

*Attesting Officer*  Acting Commissioner of Patents and Trademarks